(12) United States Patent
Yamakawa et al.

(10) Patent No.: US 7,150,733 B2
(45) Date of Patent: Dec. 19, 2006

(54) DISPOSABLE DIAPER

(75) Inventors: Shie Yamakawa, Kagawa-ken (JP); Yusuke Kawakami, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/125,217

(22) Filed: May 10, 2005

(65) Prior Publication Data

US 2005/0256492 A1    Nov. 17, 2005

(30) Foreign Application Priority Data

May 12, 2004   (JP)   ............................. 2004-142678

(51) Int. Cl.
A61F 13/15   (2006.01)
A61F 13/20   (2006.01)

(52) U.S. Cl. ................................. 604/397; 604/385.14

(58) Field of Classification Search ........... 604/385.15, 604/380, 367, 378, 385.29, 385.14, 397, 604/398, 402
See application file for complete search history.

(56) References Cited

U.S. PATENT DOCUMENTS

| | | | | |
|---|---|---|---|---|
| 2,450,059 A * | 9/1948 | Rickerson | .................... | 604/397 |
| 2,571,357 A * | 10/1951 | Gemora | ....................... | 604/397 |
| 2,683,457 A * | 7/1954 | Cunningham | ................ | 604/397 |
| 4,496,360 A * | 1/1985 | Joffe et al. | ................... | 604/397 |
| 4,928,323 A * | 5/1990 | Nathan | ........................... | 2/406 |
| 5,037,418 A * | 8/1991 | Kons et al. | .................. | 604/387 |
| 5,207,662 A * | 5/1993 | James | .................... | 604/385.25 |
| 5,392,467 A * | 2/1995 | Moretz et al. | .................. | 2/400 |
| 5,458,591 A * | 10/1995 | Roessler et al. | ............. | 604/364 |
| 5,540,672 A * | 7/1996 | Roessler et al. | ........ | 604/385.26 |
| 5,649,919 A * | 7/1997 | Roessler et al. | ........ | 604/385.29 |
| 5,711,034 A * | 1/1998 | Cillik | ............................ | 2/406 |
| 5,810,798 A * | 9/1998 | Finch et al. | ................. | 604/378 |
| 5,836,930 A * | 11/1998 | Lantz et al. | ................. | 604/378 |
| 5,853,403 A * | 12/1998 | Tanzer et al. | ........... | 604/385.09 |
| 5,873,870 A * | 2/1999 | Seitz et al. | ............. | 604/385.04 |
| 5,947,947 A * | 9/1999 | Tanzer et al. | ......... | 604/385.101 |
| 5,993,433 A * | 11/1999 | St. Louis et al. | ....... | 604/385.27 |
| 6,020,535 A * | 2/2000 | Blenke et al. | ............. | 604/367 |
| 6,049,023 A * | 4/2000 | Blenke et al. | ............. | 604/365 |
| 6,129,720 A * | 10/2000 | Blenke et al. | ......... | 604/385.16 |
| 6,254,583 B1 * | 7/2001 | Coates | .................. | 604/385.14 |
| 6,296,628 B1 * | 10/2001 | Mizutani | ..................... | 604/387 |
| 6,383,170 B1 * | 5/2002 | Mishima et al. | ....... | 604/385.19 |
| 6,406,469 B1 * | 6/2002 | Brain et al. | ................. | 604/394 |

(Continued)

FOREIGN PATENT DOCUMENTS

JP    2003-116910    4/2003

*Primary Examiner*—Tatyana Zalukaeva
*Assistant Examiner*—Paula L. Craig
(74) *Attorney, Agent, or Firm*—Lowe Hauptman & Berner LLP

(57) ABSTRACT

A diaper is provided in a transverse middle of a crotch region with a pad seat formed from top- and backsheets. The pad seat has a pair of extensions bifurcated from a rear end of the pad seat toward respective tape fasteners. In the course of wearing the diaper as well as during use of the diaper, a tensile force functioning to pull side flaps outward as viewed in a transverse direction of the article is transmitted to the respective extensions and pulls the pad seat so that the pad seat may be tightened so as to press a pad laid in the pad seat against the wearer's skin.

20 Claims, 14 Drawing Sheets

U.S. PATENT DOCUMENTS

| | | | |
|---|---|---|---|
| 6,423,043 B1 * | 7/2002 | Gustafsson | 604/385.01 |
| 6,423,047 B1 * | 7/2002 | Webster | 604/385.15 |
| 6,471,682 B1 * | 10/2002 | Kashiwagi | 604/385.27 |
| 6,652,504 B1 * | 11/2003 | Olson et al. | 604/385.25 |
| 6,677,498 B1 * | 1/2004 | Chen et al. | 604/378 |
| 6,680,423 B1 * | 1/2004 | Tanzer | 604/380 |
| 6,682,512 B1 * | 1/2004 | Uitenbroek et al. | 604/385.16 |
| 6,682,514 B1 * | 1/2004 | Brunner | 604/385.24 |
| 6,716,205 B1 * | 4/2004 | Popp et al. | 604/385.24 |
| 6,764,477 B1 * | 7/2004 | Chen et al. | 604/385.14 |
| 6,830,566 B1 * | 12/2004 | Kuen et al. | 604/396 |
| 2002/0010452 A1 * | 1/2002 | Dupuy | 604/385.14 |
| 2002/0091368 A1 * | 7/2002 | LaVon et al. | 604/385.14 |
| 2002/0169432 A1 * | 11/2002 | Fell et al. | 604/385.14 |
| 2002/0173764 A1 * | 11/2002 | Takino et al. | 604/385.28 |
| 2005/0256491 A1 * | 11/2005 | Watanabe et al. | 604/385.25 |

* cited by examiner

DISPOSABLE DIAPER

RELATED APPLICATIONS

The present application is based on, and claims priority from, Japanese Application Number 2004-142678, filed May 12, 2004, the disclosure of which is hereby incorporated by reference herein in its entirety.

BACKGROUND OF THE INVENTION

The present invention relates to disposable diapers of open-type adapted to be worn with body waste absorbing and retaining pad carried thereon.

There have been known disposable diapers of open-type defining a front waist region, a rear waist region and a crotch region extending between these waist regions. The diapers comprise a liquid-pervious topsheet, a liquid-impervious backsheet and a liquid-absorbent core interposed between these sheets and extending between the front and rear waist region. A pair of end flaps extend in a transverse direction of the diaper outside longitudinally opposite ends of the core and a pair of side flaps extend outside transversely opposite side edges of the core. The diaper is adapted to be worn with a body waste care pad laid on the topsheet. One of such diapers are disclosed, for example, in Japanese Unexamined Patent Application Publication No. 2003-116910 (hereinafter referred to as "Reference").

In the diaper of disclosed in Reference, the crotch region is formed in its transverse middle with a depressed zone in which the pad is to be laid. The depressed zone is formed from the top- and backsheets except the core and has an elliptical shape which is relatively long in the longitudinal direction. The depressed zone is provided along its peripheral edge with a circularly extending stretchable elastic member contractably attached thereto. A pair of tape fasteners is attached to the side flaps in the rear waist region, respectively, and extends in the transverse direction. Contractile force of the elastic member functions to reduce an area of the depressed zone and thereby to further depress this zone in a thickness direction of the diaper so that the pad can be securely laid in the depressed zone. Consequently, it is unlikely that the pad might be out of alignment during use of the diaper. To wear the diaper disclosed in Reference, the pad is laid in the depressed zone, then the side flaps in the rear waist region are placed upon outsides of the respective side flaps in the front waist region, and free ends of the respective tape fasteners are fastened to the outer surface of the front waist region while the tape fasteners are pulled outward in the transverse direction to connect the front and rear waist regions with each other. Upon connection of the front and rear waist regions, the diaper is formed with a waist-hole and a pair of leg-holes.

In the case of the diaper disclosed in Reference, the side flaps in the rear waist region are pulled outward in the transverse direction as the free ends of the respective tape fasteners are fastened to the outer surface of the front waist region to wear the diaper. Once the front and rear waist regions having been connected with each other by means of the tape fasteners around the wearer's body, these side flaps in the front and rear waist regions pull one another to be strained outward in the transverse direction. While the side flaps continue to be strained outward in the transverse direction in the course of wearing the diaper as well as during use of the diaper, a tensile force exerted upon these side flaps is not transmitted to the elliptical depressed zone so efficiently to pull the depressed zone outward in the transverse direction and thereby to keep the depressed zone strained outward in the transverse direction. Consequently, the depressed zone remains slack down in the thickness direction of the diaper in the course of wearing the diaper as well as during use of the diaper, making it impossible for this known diaper to press the pad laid in the depressed zone against the wearer's skin. So far as the pad is not in close contact with the wearer's skin, a clearance is left between the pad and the wearer's skin and body waste can not be reliably absorbed and retained by the pad.

SUMMARY OF THE INVENTION

It is an object of the present invention to provide disposable diapers of open-type improved so that the body waste care pad can be kept in close contact with the wearer's skin and body waste can be reliably absorbed and contained by the pad.

The present invention is directed to a disposable diaper of open-type having a front waist region, a rear waist region and a crotch region extending between these waist regions, the diaper comprising a skin-faciable liquid-pervious topsheet, a skin-opposite liquid-impervious sheet and a liquid-absorbent core of a given thickness interposed between these sheets and extending between the front and rear waist regions. The diaper is formed with a pair of end flaps extending in a transverse direction outside longitudinally opposite ends of the core and a pair of side flaps extending in a longitudinal direction outside transversely opposite side edges of the core and the side flaps in the rear waist region being provided with tape fasteners attached thereto so as to extend in the transverse direction so that the diaper is worn with a body waste care pad laid on the topsheet after the tape fasteners have been anchored on outer surface of the front waist region to connect the front and rear waist regions with each other.

The front and rear waist regions and the crotch region or at least the crotch region are or is provided along a transverse middle thereof with a pad seat formed by a cavity defined in a middle zone of said core and portions of the top- and backsheets located in the cavity $39a$ and extending in the longitudinal direction and the pad seat includes a pair of first extensions bifurcated from a rear end of the pad seat lying on the side of the rear waist region and extending toward the tape fasteners.

The present invention may include the following preferred embodiments.

The pad seat includes a pair of second extensions bifurcated from a front end of the pad seat lying on a side of the front waist region and extending toward a pair of corners defined by crossing points of the end flaps and the side flaps in the front waist region.

The pad seat is provided in a vicinity of side edges thereof with stretch- and contractable elastic members contractably attached thereto so as to extend in the longitudinal direction.

The stretch- and contractable elastic members fully extend over the pad seat and longitudinally opposite ends of the elastic members extend under the lower surfaces of respective the cores lying in the front and rear waist regions.

The stretch- and contractable elastic members respectively describe generally circular arcs which are convex inward as viewed in the transverse direction of the pad seat so that a dimension by which the elastic members are spaced from each other in the transverse direction is minimized at a longitudinal middle of the pad seat.

The stretch- and contractable elastic members extend into the first and second extensions of the pad seat.

The stretch- and contractable elastic members have tensile stress in a range of 0.05 to 4.0 N.

The topsheet extends along an inner peripheral wall of the core surrounding the pad seat from the upper surface toward the lower surface of the core, the top- and backsheets constituting the pad seat are bonded to each other on the side of the lower surface of the core and a difference in level in proportion to a thickness dimension of the core is formed between the upper surface of the core and the pad seat.

The disposable diaper according to the present invention is primarily characterized in that, in the course of wearing the diaper by anchoring the free ends of the respective tape fasteners on the outer surface of the front waist region as well as during use of the disposable diaper with the front and rear waist regions connected to each other by means of the tape fasteners, the tensile force functioning to pull the side flaps in the rear waist region outward in the transverse direction is transmitted to the first extensions so as to tighten the segment of the pad seat extending in the rear waist region and thereby to press the pad against the wearer's skin. As used herein "tighten the segment of the pad seat" means that slack and/or wrinkle is took up and held in a strained state. This diaper ensures the pad to be held in close contact with the wearer's skin in the course of wearing the diaper as well as during use of the diaper without leaving any clearance between the pad and the wearer's skin and thereby ensures body waste to be reliably absorbed and contained by the pad.

In the case of the diaper wherein the pad seat includes a pair of second extensions bifurcated from a front end of the pad seat lying on the side of the front waist region and extending toward a pair of corners defined by crossing points of the end flaps and the side flaps in the front waist region, the tensile force functioning to pull the side flaps outward in the transverse direction is transmitted to the first extensions in the course of wearing the diaper as well as during use of the diaper. During use of the diaper, the tensile force functioning to pull the side flaps in the front waist region is transmitted to the second extensions so as to tighten the segment of the pad seat extending in the front waist region and thereby to press the pad laid in the pad seat against the wearer's skin. This diaper ensures the pad to be held in close contact with the wearer's skin without leaving any clearance between the pad and the wearer's skin and thereby ensures body waste to be reliably absorbed and contained by the pad.

In the case of the diaper wherein the pad seat is provided in the vicinity of side edges thereof with stretch- and contractable elastic members contractably attached thereto so as to extend in the longitudinal direction, the contractile force of the elastic members raises the pad seat toward the wearer's skin and thereby presses the pad laid in the pad seat against the wearer's skin. In this way, the pad is reliably held in close contact with the wearer's skin so that body waste can be reliably absorbed and contained by the pad. This diaper ensures that, in the course of wearing the diaper as well as during use of the diaper, the pad seat is pulled by the tensile force exerted on the side flaps and the pad seat strained in this manner causes the elastic members to be stretched. In other words, tightening of the pad seat and contractile force of the elastic members exerted on the pad seat can be efficiently utilized to hold the pad in close contact with the wearer's skin.

In the diaper wherein the stretch- and contractable elastic members fully extend over the pad seat and longitudinally opposite ends of the elastic members extend under the lower surfaces of the respective cores lying in the front and rear waist regions, tightening of the pad seat and contractile force of the elastic members can be effectively utilized to press the pad against the wearer's skin. In addition, contractile force of the elastic members causes the cores lying in the front and rear waist regions to be pressed against the wearer's skin and to hold these cores also in close contact with the wearer's body. This diaper ensures that, even if any amount of body waste leaks out from the pad, such amount of body waste is reliably absorbed and retained by the cores lying in the front and rear waist regions. In this way, there is no anxiety that any amount of body waste might leak off from the diaper.

In the case of the diaper wherein the stretch- and contractable elastic members respectively describe circular arcs which are convex inward as viewed in the transverse direction of the pad seat so that a dimension by which the elastic members are spaced from each other in the transverse direction is minimized at a longitudinal middle of the pad seat, the contractile force of these elastic members may act fully on the pad seat to raise the pad seat as a whole toward the wearer's skin. Thus the pad laid in the seat can be fully pressed against the wearer's skin, ensuring body waste to be reliably absorbed and retained by the pad. In this diaper, pad seat is pulled outward in the transverse direction and tightened so that, in the course of wearing the diaper as well as during use of the diaper, the elastic members can be stretched along curves of the wearer's crotch region. In this way, tightening of the pad seat and contractile force of the elastic members acting on the pad seat may be effectively utilized to hold the pad against the wearer's skin.

In the case of the diaper wherein the stretch- and contractable elastic members extend into the first and second extensions of the pad seat, the tensile force transmitted from the side flaps to the first and second extensions functions to stretch the elastic members, in the course of wearing the diaper as well as during use of the diaper, so that tightening of the pad seat and contractile force of the elastic members exerted on the pad seat may be effectively utilized to hold the pad in close contact with the wearer's skin.

In the case of the diaper wherein the stretch- and contractable elastic members have tensile stress in a range of 0.05 to 4.0 N, the contractile force of the elastic members exerted on the pad seat is sufficient to raise the pad seat toward the wearer's skin and to hold the pad in close contact with the wearer's skin.

In the case of the diaper a difference in level in proportion to a thickness dimension of the core is formed between the upper surface of the core and the pad seat, a body weight of the wearer exerted on the pad depresses the pad downward in the thickness direction of the diaper along the difference in level. Consequently, it is unlikely that the pad might become bulky and create a feeling of discomfort against the wearer. The pad seat is tightened and maintained in such tightened state so long as the diaper is worn and, as soon as the pad is relieved of the wearer's body pressure, the pad can reliably restore its initial thickness and comes again in close contact with the wearer's skin. In this way, this diaper ensures the pad to be held in close contact with the wearer's skin and thereby ensures body waste to be reliably absorbed and retained by the pad.

DETAILED DESCRIPTION OF THE PREFERRED EMBODIMENTS

Details of a disposable diaper according to the present invention will be more fully understood from the description given hereunder with reference to the accompanying drawings.

Figure 1:
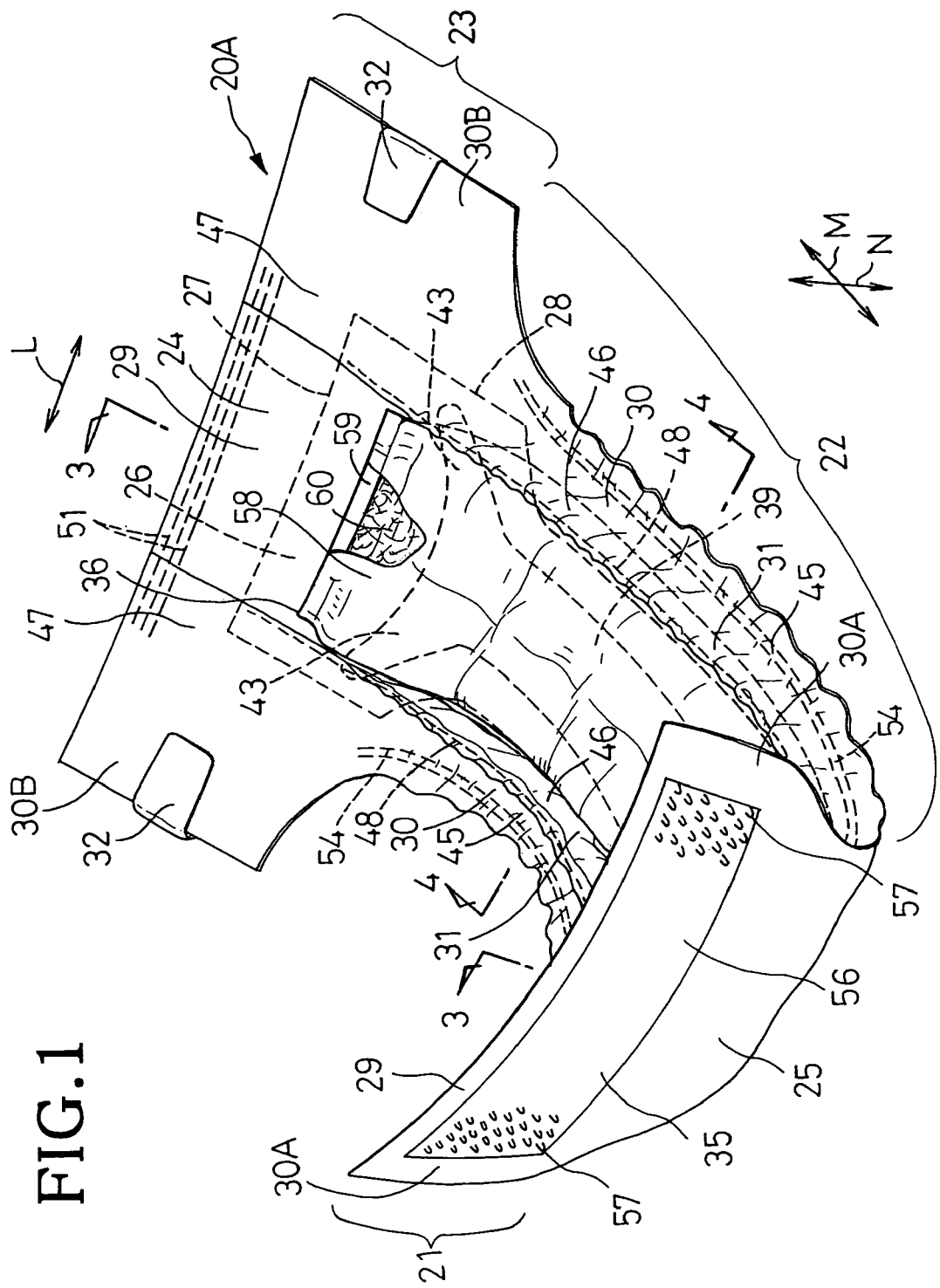
FIG. 1 is a perspective view showing a disposable diaper with the pad laid in a pad seat.
Figure 2:
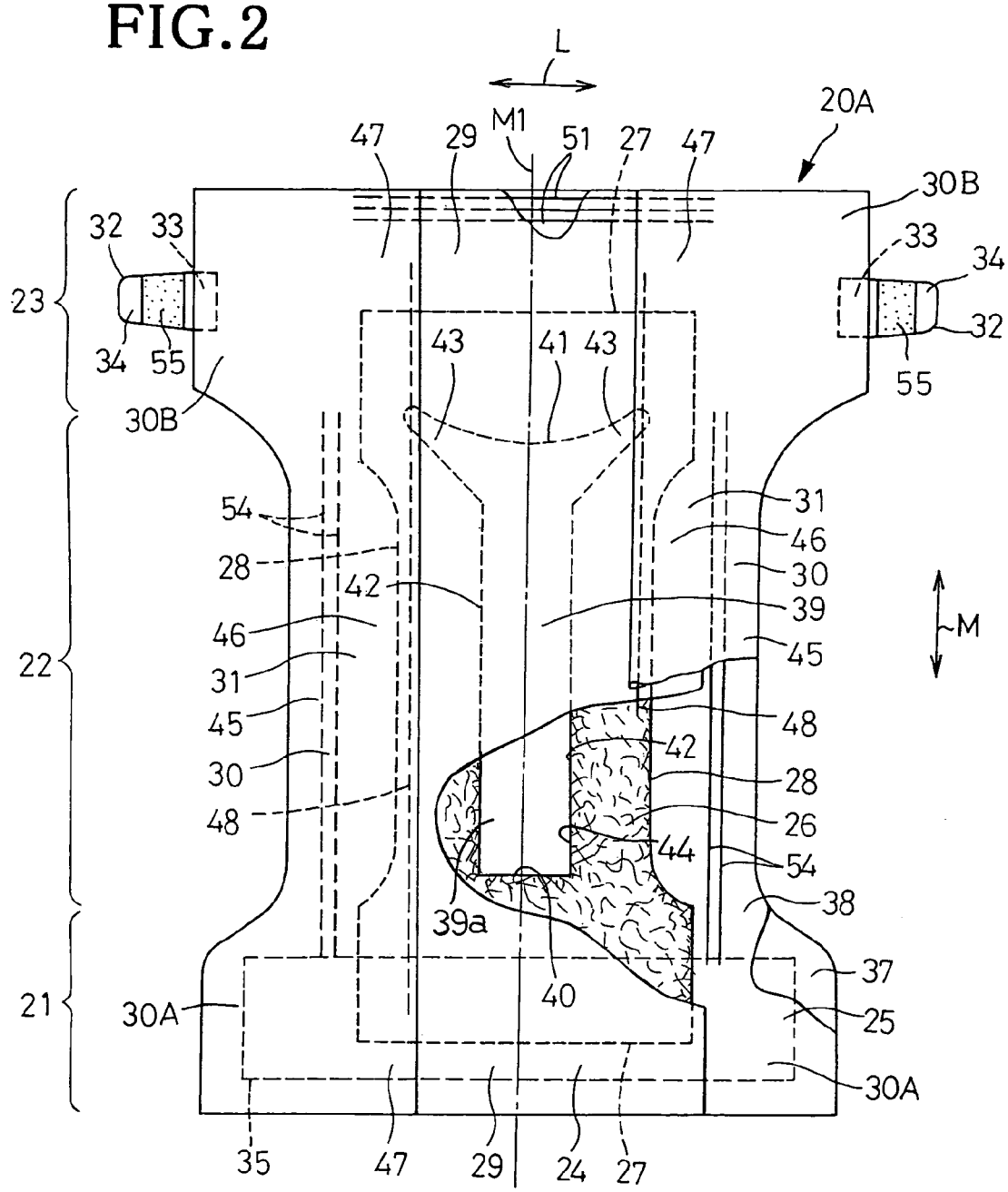
FIG. 2 is a partially cutaway plan view showing the diaper of FIG. 1 with the pad not shown.
Figure 3:
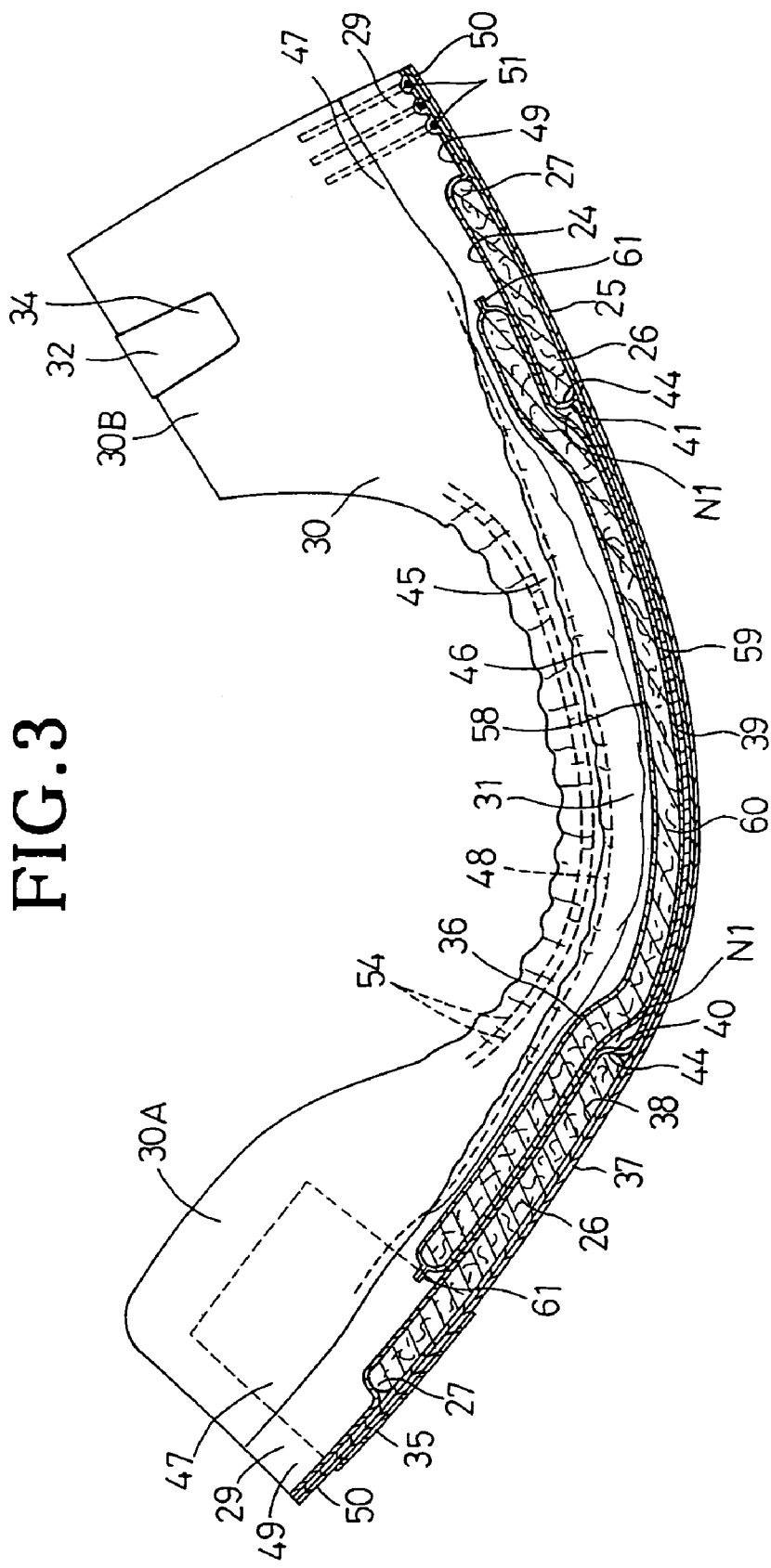
FIG. 3 is a sectional view taken along the line 3—3 in FIG. 1.
Figure 4:
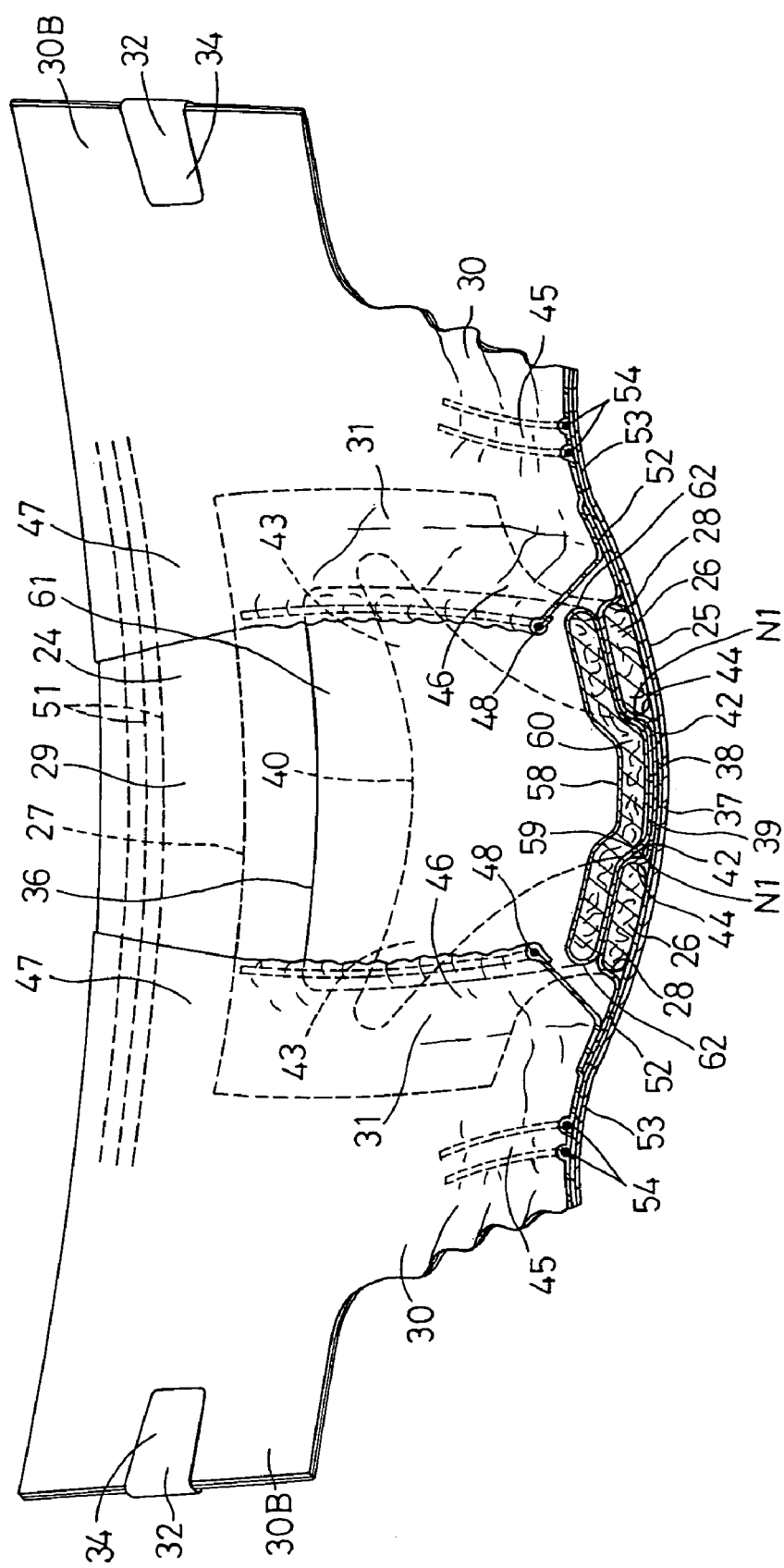
FIG. 4 is a sectional view taken along the line 4—4 in FIG. 1.

FIG. 1 is a perspective view showing a disposable diaper 20A with a pad 36 laid in a pad seat 39, FIG. 2 is a partially cutaway plan view showing the diaper 20A of FIG. 1 with the pad 36 not shown, FIG. 3 is a sectional view taken along the line 3—3 in FIG. 1 and FIG. 4 is a sectional view taken along the line 4—4 in FIG. 1. In FIGS. 1 and 2, a transverse direction is indicated by an arrow L, a longitudinal direction is indicated by an arrow M and a thickness direction is indicated by an arrow N (in FIG. 1 alone). FIG. 2 shows the diaper 20A as developed in the longitudinal direction as well as in the transverse direction against contractile force of stretch- and contractible elastic members 48, 51, 54. As used herein, "inner surfaces" of top- and backsheets 24, 25 and leak-barrier sheets 31 constituting the diaper 20A refer to the surfaces thereof facing a core 26 and "outer surfaces" of these sheets 24, 25, 31 refer to the surfaces thereof facing away from the core 26. As used herein, "upper surface" of the core 26 refers to the surface facing the topsheet 24 and "lower surface" of the core 26 refers to the surface thereof facing the backsheet 25. As used herein, "inner surfaces" of a topsheet 58 and a backsheet 59 constituting the pad 36 refer to the surfaces thereof facing a core 60 and "outer surface" of these sheets 58, 59 refer to the surfaces thereof facing away the core 60.

As viewed in the longitudinal direction, the diaper 20A has a front waist region 21, a rear waist region 23 and a crotch region 22 extending between these waist regions 21, 23. The diaper 20A comprises the skin-faciable liquid-pervious topsheet 24, the skin-opposite liquid-impervious sheet 25 and the liquid-absorbent core 26 of a given thickness interposed between the top- and backsheets 24, 25 and extending between the front and rear waist regions 21, 23. The diaper 20A is formed with a pair of end flaps 29 extending in the transverse direction outside longitudinally opposite ends 27 of the core 26 and a pair of side flaps 30 extending in the longitudinal direction outside transversely opposite side edges 28 of the core 26.

The side flaps 30 are provided with a pair of liquid-impervious leak-barrier sheets 31 extending in the longitudinal direction so as to be spaced from and opposed to each other. In the crotch region 22, the side flaps 30 curve inward as viewed in the transverse direction of the diaper 20A so as to describe generally circular arcs. Thus, the diaper 20A this has a generally hourglass-like planar shape as shown in FIG. 2. The side flaps 30B in the rear waist region 23 are respectively provided with tape fasteners 32 extending in the transverse direction. The tape fasteners 32 respectively have fixed ends 33 and free ends 34. The front waist region 21 is provided with a target tape strip 35 on which the free ends 34 of the respective tape fasteners 32 are releasably anchored. As will be understood from FIG. 1, the diaper 20A is adapted to be worn with the body waste care pad 36 laid in a depressed zone 39 as will be described later in details after the front and rear waist regions 21, 23 have been connected with each other by means of the tape fasteners 32.

The topsheet 24 is formed from a hydrophilic fibrous nonwoven fabric. The backsheet 25 is formed from a composite sheet composed of a hydrophobic fibrous nonwoven fabric 37 and a breathable liquid-impervious plastic film 38 laminated together. The leak-barrier sheets 31 are formed from a water repellent finished hydrophobic fibrous nonwoven fabric. The core 26 is formed from a mixture of particulate or fibrous superabsorbent polymers and fluff pulp fibers or a mixture of particulate or fibrous superabsorbent polymers, fluff pulp fibers and thermoplastic synthetic resin fibers, in any case, compressed to a thickness required to have a stiffness higher than those of the top- and backsheets 24, 25 and the leak-barrier sheets 31. The core 26 is entirely wrapped with a tissue paper (not shown) in order to prevent the core 26 from getting out of its initial shape. The core 26 is bonded to the respective inner surfaces of the top- and backsheets 24, 25.

The crotch region 22 is formed in its transverse middle with a pad seat 39 extending in the longitudinal direction. The pad seat 39 is formed by a cavity 39a defined in a middle zone of the core 26 and portions of the top- and backsheets 24, 25 located in the cavity 39a. The cavity 39a is contoured by a periphery consisting of a front end 40 extending in the transverse direction in the front waist region 21, a rear end 41 extending in the transverse direction in the rear waist region 41 and side edges 42 extending in the longitudinal direction between these front and rear ends 40, 41. The pad seat 39 has a pair of first extensions 43 bifurcated from the rear end 41 and extending toward the respective tape fasteners 32. The extensions 43 obliquely extend from the rear end 41 of the pad seat 39 toward the respective tape fasteners 32 so as to be gradually spaced from a longitudinal centerline M1 bisecting a transverse dimension of the diaper 20A. In addition, these extensions 43 are tapered from the rear end 41 of the pad seat 39 toward the respective tape fasteners 32. The pad seat 39 including the extensions 43 is defined by segments of the top- and backsheets 24, 25 not including the core 26 and surrounded by an inner peripheral wall 44 of the core 26. A segment of the pad seat 39 including the extensions 43 has a stiffness lower than that of the remaining segment of the pad seat 39 in which the core 26 is present.

In the pad seat 39, the topsheet 24 extends along the inner peripheral wall 44 surrounding the pad seat 39 from the upper surface toward the lower surface of the core 26 and the inner surface of the topsheet 24 is bonded to the inner peripheral wall 44 of the core 26. On the side of the lower surface of the core 26, the top- and backsheets 24, 25 forming the pad seat 39 have the respective inner surfaces bonded to each other in an intermittent manner. The pad seat 39 is depressed in the thickness direction of the diaper 20A. A difference in level N1 in proportion to a thickness dimension of the core 26 is formed between the upper surface of the core 26 and the pad seat 39.

The leak-barrier sheets 31 are provided on the side of the outer surface of the topsheet 24. These leak-barrier sheets 31 have proximal zones 45 extending in the longitudinal direction on the side flaps 30, distal zones 46 extending in the longitudinal direction in parallel to the proximal zones 45 and normally biased to rise up above the topsheet 24 and longitudinally opposite ends 47 lying on the end flaps 29 and collapsed inward as viewed in the transverse direction of the diaper 20A. The proximal zones 45 as well as the distal zones 46 extend between the end flaps 29. The distal zones 46 are provided, in the vicinity of respective uppermost edges, with stretch- and contractable elastic members 48 contractably attached thereto so as to extend in the longitudinal direction. Specifically, these elastic members 48 are secured to the respective distal zones 46 with adhesives under tension at a given ratio in the longitudinal direction. These elastic members 48 contract and the distal zones 46 also contract in the longitudinal direction as the diaper 20A is left to curve inward. Consequently the distal zones 46 rise up above the topsheet 24 to form barriers against body waste.

Respective end portions 49, 50 of the top- and backsheets 24, 25 extending in the longitudinal direction outward beyond the ends 27 of the core 26 cooperate with the ends 47 of the leak-barrier sheets 31 to define the end flaps 29. In each of the end flaps 29, the respective end portions 49, 50 of the top- and backsheets 24, 25 are overlapped with the ends 47 of the leak-barrier sheets 31 wherein the top- and backsheets 24, 25 have the respective inner surfaces bonded together and the outer surface of the topsheet 24 is bonded to the inner surfaces of the respective leak-barrier sheets 31. The end flap 29 in the rear waist region 23 is provided with a plurality of waist-surrounding elastic members 51 contractably secured thereto so as to extend in the transverse direction with adhesives. These waist-surrounding elastic members 51 are interposed between the respective ends 49, 50 of the top- and backsheets 24, 25 and secured to the respective sheets 24, 25 of these sheets 24, 25 with adhesives under tension at a given ratio in the transverse direction.

Respective side edge portions 52, 53 of the top- and backsheets 24, 25 extending in the transverse direction outward beyond the side edges 28 of the core 26 cooperate with the proximal zones 45 of the respective leak-barrier sheets 31 to define the side flaps 30. In each of the side flaps 29, the side edge portion 52 of the topsheet 24 extends in the transverse direction outward slightly beyond the side edge 28 of the core 26 while the side edge portion 53 of the backsheet 25 as well as the proximal zone 45 of the leak-barrier sheet 31 extend in the transverse direction outward beyond the side edge portion 52 of the topsheet 24. In each of the side flaps 30, the respective side edge portions 52, 53 of the top- and backsheets 24, 25 are overlapped with the proximal zone 45 of the leak-barrier sheet 31 wherein the top- and backsheets 24, 25 have the respective inner surfaces bonded together and the inner surface of the topsheet 24 and the outer surface of the backsheet 25 are bonded to the inner surface of the leak-barrier sheet 31. Each of the side flaps 30 is provided with a plurality of leg-surrounding elastic members 54 contractably attached with adhesives thereto. In each of the side flaps 30, the leg-surrounding elastic members 54 are interposed between the side edge portion 53 of the backsheet 25 and the proximal zone 45 of the leak-barrier sheet 31 and bonded to the respective inner surface of these sheets 25, 31 with tension at a given ratio in the longitudinal direction.

The tape fastener 32 is formed from a fibrous nonwoven fabric. The fixed end 33 of the tape fastener 32 is interposed between the side edge portion 53 of the backsheet 25 and the proximal zone 45 of the leak-barrier sheet 31 and bonded to the respective inner surfaces of these sheets 25, 31. The tape fastener 32 is provided on the free end 34 with a hook member 55. In a state of the tape fastener 32 illustrated in FIG. 1, the free end 34 is folded inward as viewed in the transverse direction of the diaper 20A and temporarily held on the side flap 30B (i.e., on the outer surface of the leak-barrier sheet 31). It should be understood that the hook member 55 may be replaced by a pressure-sensitive adhesive coated on the free end 34 and protectively covered with a release sheet. The target tape strip 35 comprises a base 56 and a loop member 57 protuberated from the base 56 and has a rectangular shape which is relatively long in the transverse direction. The base 56 constituting the target tape strip 35 is bonded to the outer surface of the backsheet 25. When it is desired to coat the free end 34 of the tape fastener 32 with a pressure-sensitive adhesive, the target tape strip 35 is preferably formed from a plastic film.

The pad 36 comprises a wearer-faciable liquid-pervious topsheet 58, a wearer-opposite liquid-impervious backsheet 59 and a liquid-absorbent core 60 of a given thickness interposed between these top- and backsheets 58, 59 and bonded to respective inner surfaces of these sheets 58, 59. The pad 36 has a rectangular shape which is relatively long in the longitudinal direction and contoured by longitudinally opposite ends 61 extending in the transverse direction and transversely opposite side edges 62 extending in the longitudinal direction. Along the ends as well as along the side edges 62, the top- and backsheets 58, 59 are overlapped together and have respective inner surfaces bonded to each other. The topsheet 58 is formed from a hydrophilic fibrous nonwoven fabric and the backsheet 59 is formed from a hydrophobic fibrous nonwoven fabric. The core 60 is formed from a mixture similar to the mixture forming the core 26 provided integrally with the diaper 20A. The mixture destined to form the core 60 is also entirely wrapped with a tissue paper (not shown). It is also possible to form the pad 36 from such liquid-absorbent core 60 entirely wrapped with a liquid-pervious sheet.

Figure 5:
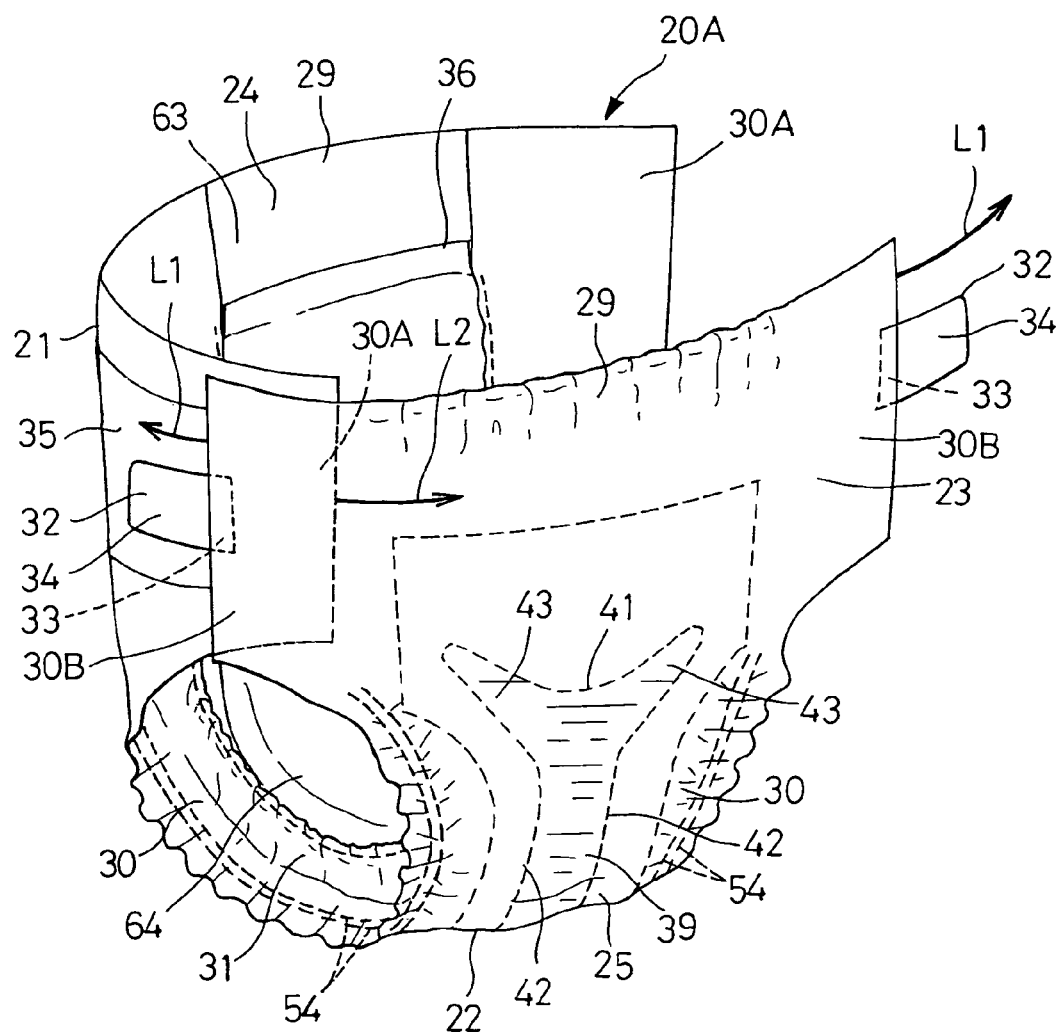
FIG. 5 is a perspective view illustrating the sequence in which the diaper is worn.

FIG. 5 is a perspective view illustrating a sequence in which the diaper 20A is worn. FIG. 5 shows the diaper 20A as viewed from the side of the rear waist region 23. FIG. 5 shows one of the tape fasteners 32 anchored on the target tape strip 35 without showing the wearer. This diaper 20A is worn in the sequence as follows: The pad 36 is laid in the pad seat 39 so that the backsheet 59 of the pad 36 may be put in contact with the topsheet 24 of the diaper 20A. Then, the wearer' buttock is placed on the rear waist region 23 and the diaper 20A is folded upward along the crotch region 22 to place the front waist region 21 on the wearer's abdominal region. Now the tape fasteners 32 may be pulled outward in the transverse direction with the respective free ends 34 held by the fingers until the side flaps 30B in the rear waist region 23 are placed upon the respective outer sides of the side flaps 30A in the front waist region 21 and then the free ends 34 of the respective tape fasteners 32 are anchored on the target tape strip 35 (i.e., on the outer surface of the front waist region 21) by means of the hook members to connect the front and rear waist regions 21, 23 with each other. Upon connection of these front and rear waist regions 21, 23, the diaper 20A is formed with a waist-hole 63 and a pair of leg-holes 64 below the waist-hole 63. Of the diaper 20A worn in this manner, the front waist region 21 comes in contact with the wearer's abdominal region, the crotch region 22 comes in contact with the wearer's crotch region and the rear waist region 23 comes in contact with the wearer's buttock and back.

In the course of wearing the diaper 20A completed by anchoring the respective tape fasteners 32 on the target tape strip 35, the side flaps 30B in the rear waist region 23 are pulled outward in the transverse direction indicated by an arrow L1 in FIG. 5 and the tensile force functioning to pull the side flaps 30B outward in the transverse direction is transmitted to the first extensions 43. It is also true during use of the diaper 20A having the front and rear waist regions 21, 23 connected with each other by the tape fasteners 32 in this manner. Specifically, the side flaps 30A in the front waist region 21 and the side flaps 30B in the rear waist region 23 pull each other so that the side flaps 30A, 30B are pulled outward in the transverse direction as indicated by the arrows L1, L2 in FIG. 5 and the tensile force functioning to pull the side flaps 30B outward in the transverse direction is transmitted to the first extensions 43. The segment of the pad seat 39 including the first extensions 43 has a stiffness lower than a stiffness of the remaining segment in which the core 26 is present and, in addition, the extensions 42 extend toward the respective tape fasteners 32. Such a unique arrangement ensures that the tensile force exerted on the side flaps 30B in the course of wearing the diaper 20A and during use of the diaper 20A is reliably transmitted from the side flaps 30B to the respective extensions 43 to tighten the pad seat 39 (i.e., to pick up slack and wrinkle of the pad seat 39). The pad 36 is pressed against the wearer's skin as the pad seat 39 is tightened in this manner. In this way, it is ensured that body waste discharged in the diaper worn is reliably absorbed by the core through the topsheet 58 of the pad 36.

In the course of wearing the diaper 20A as well as during use of the diaper 20A, the pad 36 is reliably pressed against the wearer's skin, leaving no clearance between the pad 36 and the wearer's skin so that body waste can be reliably absorbed and contained by the pad 36. Should body waste partially leak from the pad seat 39, such leakage of body waste can be absorbed and contained by the core 26 which is present around the pad seat 39. In this way, leakage of body waste from the diaper 20A can be reliably avoided.

A body weight of the wearer exerted on the pad 36 depresses the pad 36 downward in the thickness direction of the diaper 20A along the difference in level N1. Consequently, it is unlikely that the pad 36 might become bulky and create a feeling of discomfort against the wearer. The pad seat 39 is tightened and maintained in such a tightened state so long as the diaper 20A is worn and, as soon as the pad 36 is relieved of the wearer's body pressure, the pad 36 can reliably restore its initial thickness and comes again in close contact with the wearer's skin.

The segment of the pad seat 39 including the first extensions 43 has a stiffness value in a range of 0.1 to 2.0 mN·cm, preferably, in a range of 0.8 to 1.5 mN·cm. If the stiffness of the pad seat 39 exceeds 2.0 mN·cm, it will be difficult for the tensile force exerted on the side flaps 30B to tighten the pad seat 39 and sometimes to press the pad 36 against the wearer's skin even if such tensile force is transmitted to the pad seat 39. The stiffness value was measured in pursuance of Gurley's Method (JIS L 1096-01-8.20.1). The measurement was carried out using a method comprising the steps as follow:

(1) The pad seat 39 was cut out from the diaper 20A to obtain samples each having a longitudinal dimension of 25 mm and a transverse dimension of 38.0 mm for measurement of stiffness values. For measurement of the stiffness values, the Gurley's Stiffness Tester was used.

(2) One of longitudinally opposite end portions of the sample was held by a chuck of the tester and the other end portion was maintained in engagement with a pendulum of the tester and the tester was initialized by loading an auxiliary weight so that the tester scale may point the readings in a range of 3 to 6. The tester was turned on and a scale reading of the moment at which the pivot rod of the pendulum was separated from the sample was recorded as a first stiffness value. Now the other of longitudinally opposite ends of the sample was held by the chuck of the tester and the opposite end was maintained in engagement with the pendulum of the tester. The tester was initialized by loading the auxiliary weight so that the tester scale may point the scale readings in a range of 3 to 6. The tester was turned on and the scale reading of the moment at which the pivot rod of the pendulum was separated from the sample was recorded as a second stiffness value. An average value of these first and second stiffness values obtained in this manner was recorded as the stiffness value of the sample. The stiffness value of the first sample was in a range of 0.1 to 2.0 mN·cm. The stiffness value of the sample was adopted as the stiffness of the pad seat 39.

Figure 6:
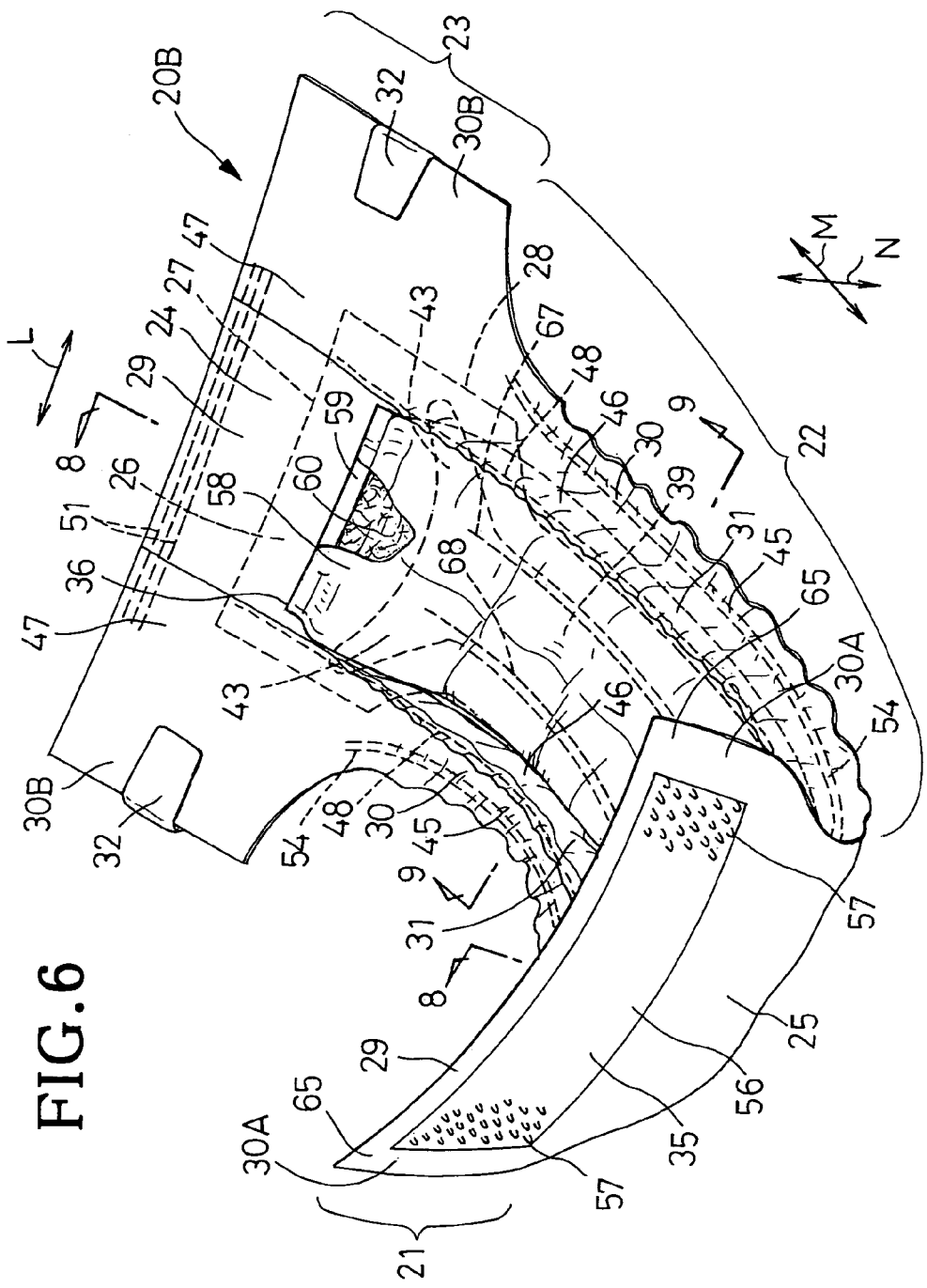
FIG. 6 is a perspective view showing one preferred embodiment of the disposable diaper with the pad laid in the pad seat.
Figure 7:
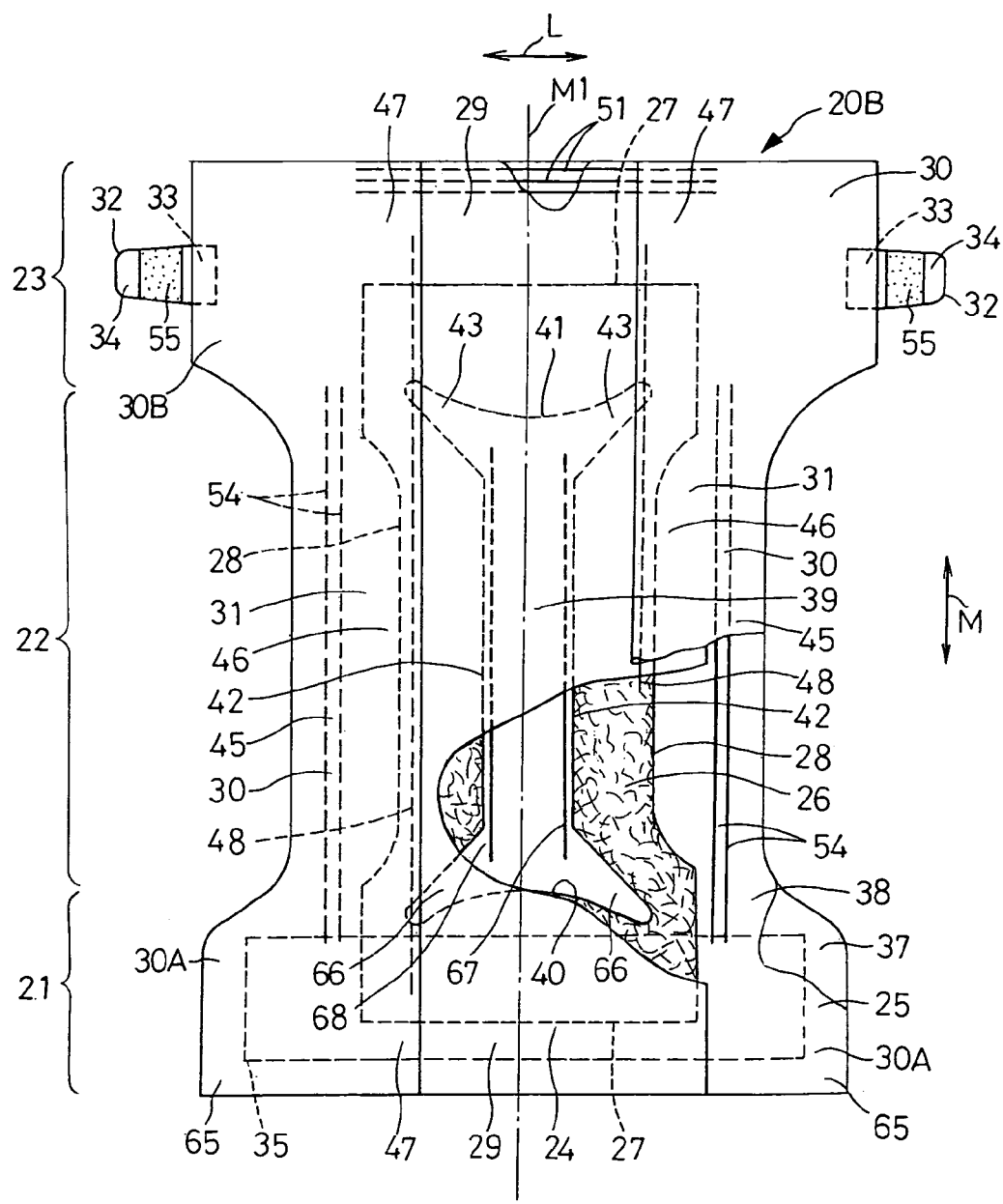
FIG. 7 is a partially cutaway plan view showing the diaper of FIG. 6 with the pad not shown.
Figure 8:
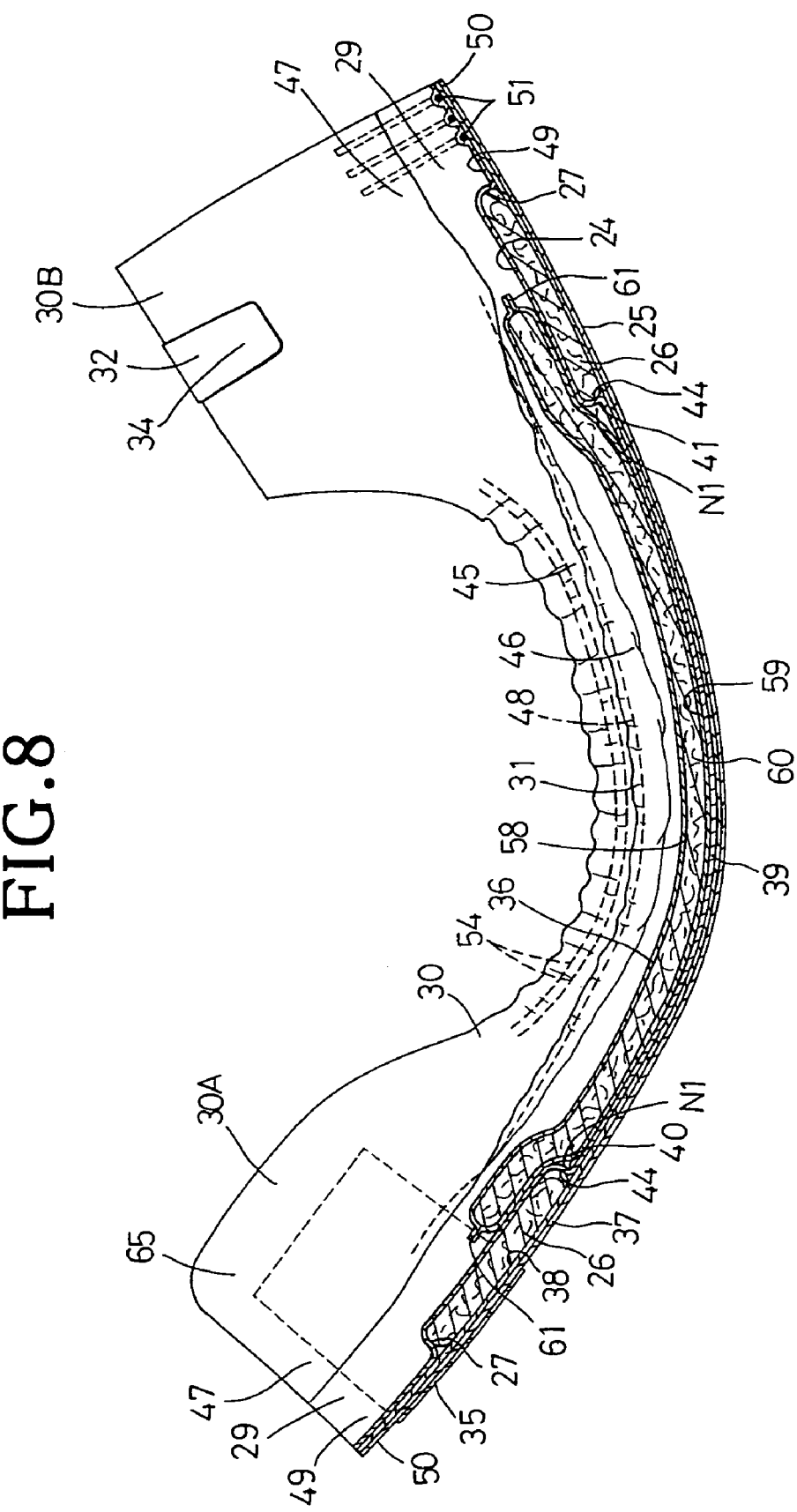
FIG. 8 is a sectional view taken along the line 8—8 in FIG. 6.
Figure 9:
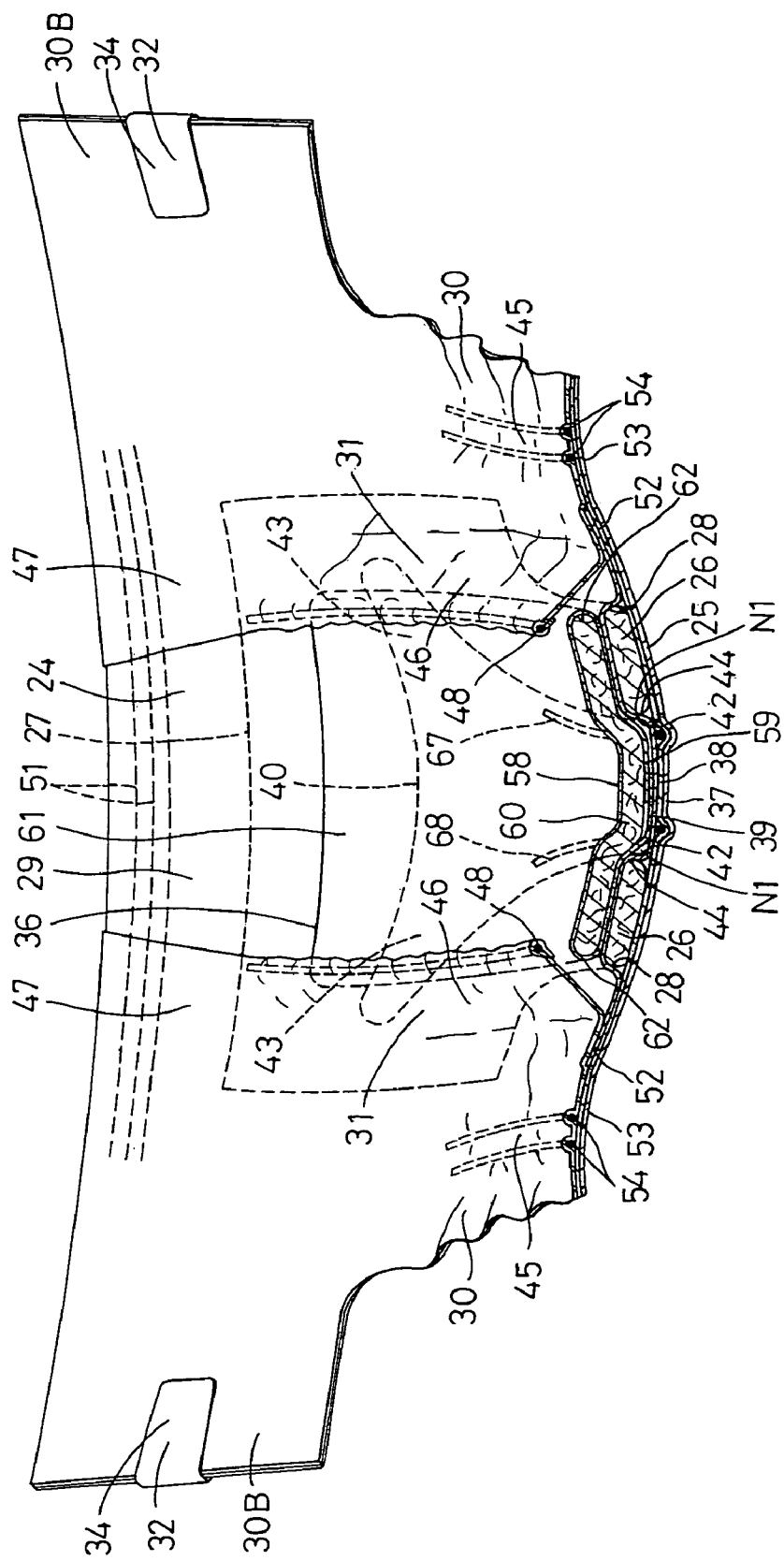
FIG. 9 is a sectional view taken along the line 9—9 in FIG. 6.

FIG. 6 is a perspective view showing the diaper 20B according to one preferred embodiment with the pad 36 laid in the pad seat 39, FIG. 7 is a partially cutaway plan view showing the diaper 20B of FIG. 6 with the pad 36 not shown, FIG. 8 is a sectional view taken along the line 8—8 in FIG. 6 and FIG. 9 is a sectional view taken along the line 9—9 in FIG. 6. In FIGS. 6 and 7, the transverse direction is indicated by the arrow L, the longitudinal direction is indicated by the arrow M and a thickness direction is indicated by the arrow N (in FIG. 6 alone). FIG. 7 shows the diaper 20B as developed in the longitudinal direction as well as in the transverse direction against contractile force of the stretch- and contractable elastic members 48, 51, 54, 66.

The diaper 20B is of open-type adapted to be worn with the front and rear waist regions 21, 23 connected to each other by means of the tape fasteners 32 after the body waste care pad 36 has been laid in the pad seat 39. Similarly to the diaper 20A of FIGS. 1–5, the diaper 20B also comprises the liquid-pervious topsheet 24, the liquid-impervious backsheet 25, the liquid-absorbent core 26 interposed between the top- and backsheets 24, 25 and extending between the front and rear waist regions 21, 23 and a pair of the liquid-impervious leak-barrier sheets 31 attached to the side flaps 30 so as to extend in the longitudinal direction. This diaper 20B is distinguished from the diaper 20A of FIGS. 1–5 in that the pad seat 39 has second extensions 66 and the pad seat 39 is provided with stretch- and contractable elastic members 67, 68. The remaining components similar to those in the diaper 20A of FIGS. 1–5 are designated by similar references and repetitive description thereof will be eliminated.

The pad seat 39 has, in addition to a pair of the first extensions 43, a pair of second extensions 66 bifurcated from the front end 40 and extending toward two corners 65 at which the end flaps 29 intersect with the side flaps 30A in the front waist region 21. The extensions 66 obliquely extend from the front end 40 of the pad seat 39 toward the respective corners 65 so as to be gradually spaced from the longitudinal centerline M1. These extensions 66 are tapered from the front end 40 toward the respective corners 65.

The pad seat 39 is provided in the vicinity of the respective side edges 42 with a stretch- and contractable first elastic member 67 (stretch- and contractable elastic member) and a stretch- and contractable elastic member 68 (stretch- and contractable elastic member) both contractably attached thereto. These elastic members 67, 68 are spaced from and opposed to each other and extend in the longitudinal direction. These elastic members 67, 68 lie between the front and rear ends 40, 41 and extend close to the first and second extensions 43, 66. These elastic members 67, 68 are interposed between the top- and backsheets 24, 25 and secured to the respective inner surfaces of these sheets 24, 25 with adhesives under tension at a given ratio in the longitudinal direction.

Figure 10:
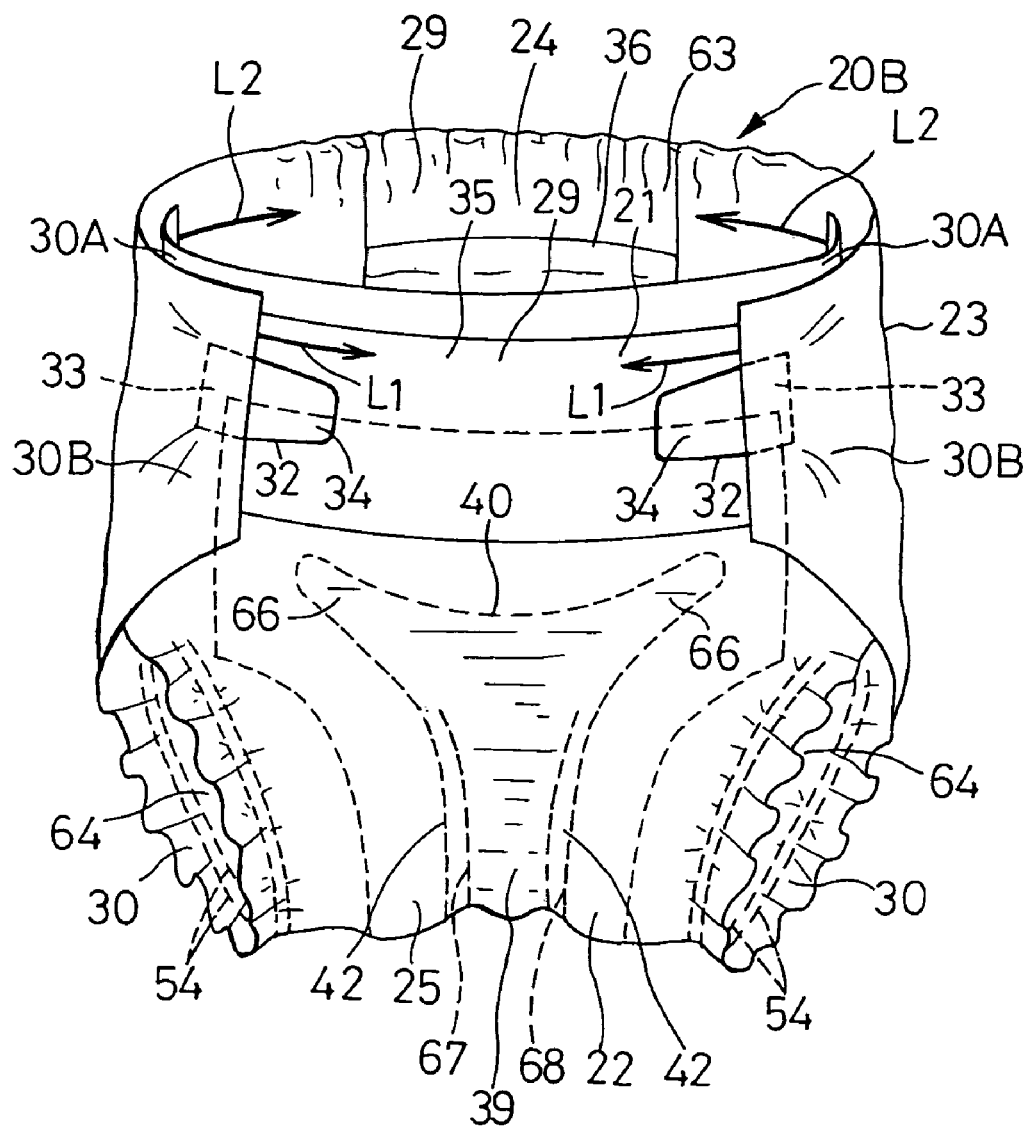
FIG. 10 is a perspective view showing the diaper of FIG. 6 put on the wearer's body as viewed from the side of the front waist region.

FIG. 10 is a perspective view showing the diaper 20B worn as viewed from the side of the front waist region 21. The sequence in which the diaper 20C is worn is the same as the wearing sequence for the diaper 20A as described in reference with FIG. 5 and will not be repetitively described here. In the course of wearing the diaper 20B completed by anchoring the respective tape fasteners 32 on the target tape strip 35, the side flaps 30B in the rear waist region 23 are pulled outward in the transverse direction indicated by the arrow L1 in FIG. 5 and the tensile force functioning to pull the side flaps 30B outward in the transverse direction is transmitted to the first extensions 43. It is also true during use of the diaper 20B having the front and rear waist regions 21, 23 connected with each other by the tape fasteners 32 in this manner. Specifically, the side flaps 30A, 30B in the front and rear waist regions 21, 23 pull each other so that the side flaps 30A, 30B are pulled outward in the transverse direction as indicated by the arrows L1, L2 in FIGS. 5, 10 and the tensile force functioning to pull the side flaps 30A, 30B outward in the transverse direction is transmitted to the first and second extensions 43, 66. The segment of the pad seat 39 including the first and second extensions 43, 66 has a stiffness lower than a stiffness of the remaining segment in which the core 26 is present and, in addition, the extensions 42 extend toward the respective tape fasteners 32 and the extensions 66 extend toward the corners 65. Such a unique arrangement ensures that the tensile force exerted on the side flaps 30A, 30B in the course of wearing the diaper 20B and during use of the diaper 20C is reliably transmitted from the side flaps 30A, 30B to the respective extensions 43, 66 to tighten the pad seat 39. The pad 36 is pressed against the wearer's skin as the pad seat 39 is tightened in this manner. In this way, it is ensured that body waste discharged on the diaper 20C worn is reliably absorbed by the core through the topsheet 58 of the pad 36.

The contractile force of the first and second elastic members 67, 68 secured to the pad seat 39 in the vicinity of the side edges 42 thereof biases the pad seat 39 to rise up toward the wearer's skin and thereby to press the pad 36 laid in the seat 39 against the wearer's skin. In this way, body waste can be reliably absorbed and retained by the pad 39. In the course of wearing the diaper 20B as well as during use of the diaper 20B, the pad seat 39 is pulled outward in the transverse direction so as to stretch the elastic members 67, 68. The pad seat 39 tightened in this manner and the contractile force of these elastic members 67, 68 may be utilized to hold the pad 36 in close contact with the wearer's skin.

The segment of the pad seat 39 including the first and second extensions 43, 66 has a stiffness value in a range of 0.1 to 2.0 mN·cm, preferably, in a range of 0.8 to 1.5 mN·cm.

If the stiffness of the pad seat 39 is less than 0.1 mN·cm, the pad seat 39 will be excessively contracted, depending on the tensile stress of the elastic member 67, under the contractile force of the elastic members 67, 68. In consequence, it will be impossible for the tensile force exerted on the side flaps 30A, 30B to tighten the pad seat 39 sufficiently to press the pad 36 against the wearer's skin even when such tensile force is more or less transmitted to the pad seat 39. If the stiffness of the pad seat 39 exceeds 2.0 mN·cm, it will be difficult for the tensile force exerted on the side flaps 30A, 30B to tighten the pad seat 39 and sometimes to press the pad 36 against the wearer's skin even when such tensile force is more or less transmitted to the pad seat 39. The stiffness value was measured in pursuance of Gurley's Method (JIS L 1096-01-8.20.1). The measurement was carried out using the same method as that used for the diaper 20A of FIGS. 1–5.

The tensile stress of the elastic members 67, 68 is in a range of 0.05 to 4.0 N, preferably, in a range of 0.08 to 4.0 N. "The tensile stress of the elastic members 67, 68" as used herein refers to the tensile stress exhibited by each component constituting these elastic members 67, 68. If the tensile stress of the elastic members 67, 68 is less than 0.05 N, the contractile force of these elastic members 67, 68 acting upon the pad seat 39 will be insufficient, depending on the stiffness value of the pad seat 39, to raise the pad seat 39 toward the wearer's skin and to press the pad 36 against the wearer's skin. If the tensile stress of the elastic members 67, 68 exceeds 4.0 N, the contractile force of the elastic members 67, 68 will excessively contract the pad seat 39 in the longitudinal direction and the tensile force exerted on the side flaps 30A, 30B will be insufficient to tighten the pad seat 39 and to press the pad 36 against the wearer's skin even when the tensile force exerted on the side flaps 30A, 30B is more or less transmitted to the pad seat 39. The tensile stress of the elastic members 67, 68 was measured by the method comprising the steps as follow:

(1) The same elastic member (single) as those used in the diaper 20B was prepared as a sample for measurement. For measurement of the tensile stress, the Tensile Tester manufactured by SHIMADZU CORPORATION was used.

(2) Transversely opposite side edge portions of the sample were clamped by respective chucks of the tensile tester (a dimension over which each end portion was clamped by the chuck: about 10 mm, a length dimension of the sample measured between the chucks: about 100 mm). The sample was stretched in the longitudinal direction at a rate of 100 mm/min and, after the sample had been stretched by 300%, the tension was relieved. The sample was stretched again in the longitudinal direction at a rate of 100 mm/min and a force exerted on the tester at the moment the sample was stretched by 200% was obtained as the tensile stress value of the sample. The tensile stress value of the sample obtained in this manner was in a range of 0.05 to 4.0 N. The tensile stress of the sample obtained in this manner was adopted as the tensile stress exhibited by the single one of the elastic members 67, 68. As used herein "the sample was stretched by 200%" means that, for example, the sample having its inter-chuck dimension of 100 mm was stretched to 100 mm×2.0=200 mm.

Figure 11:
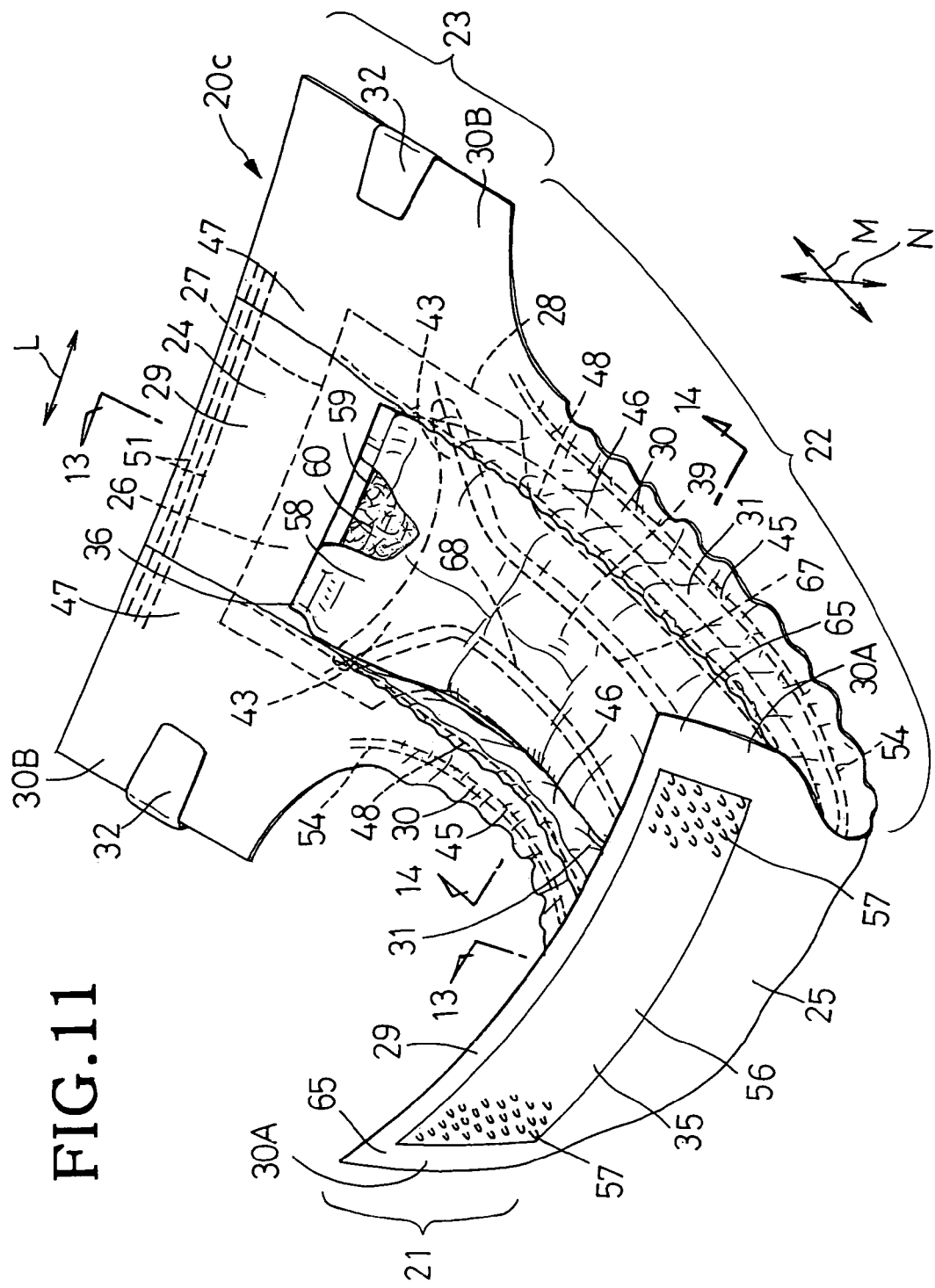
FIG. 11 is a perspective view showing another preferred embodiment of the diaper with the pad laid in the pad seat.
Figure 12:
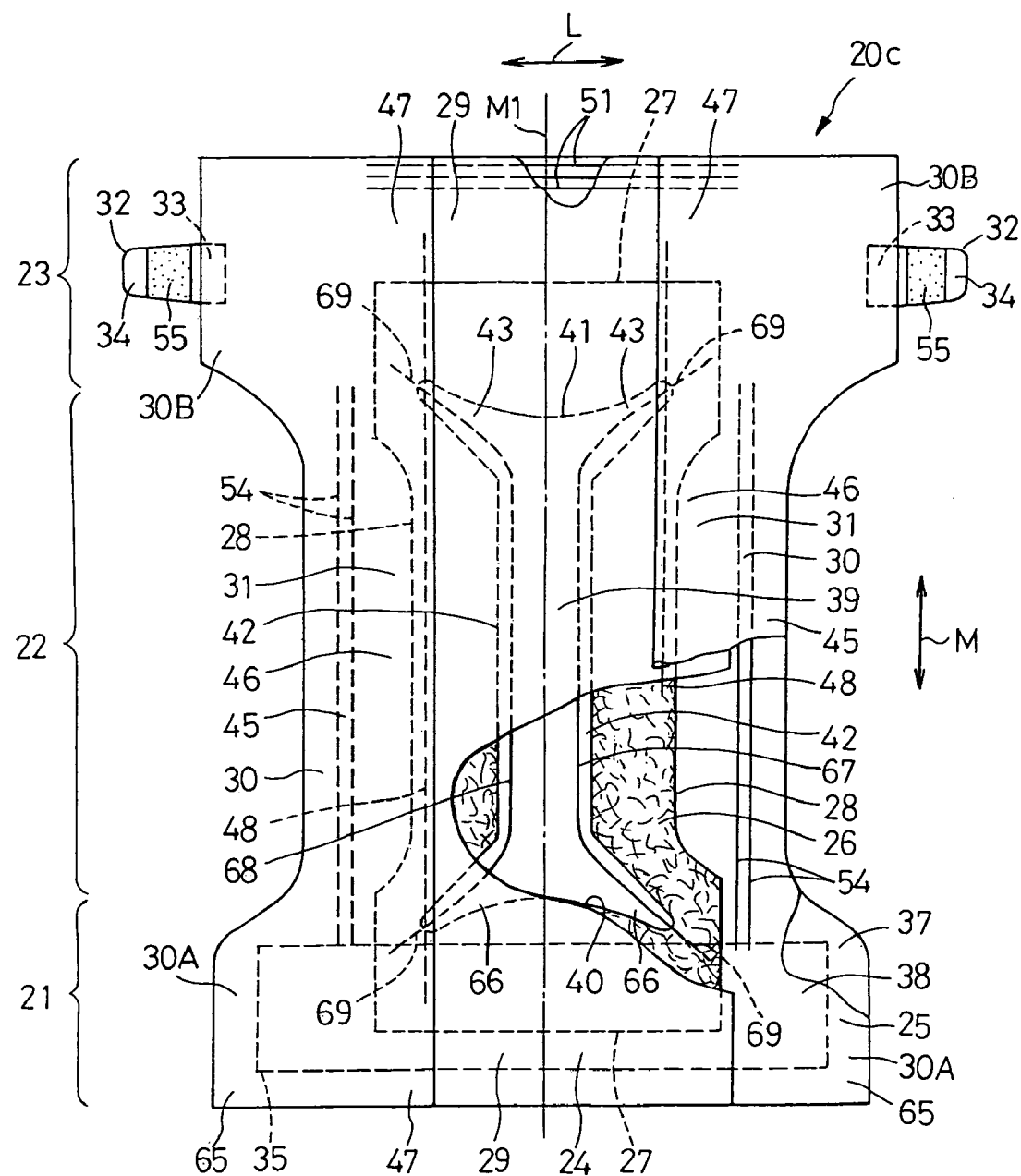
FIG. 12 is a partially cutaway plan view showing the diaper of FIG. 11 with the pad not shown.
Figure 13:
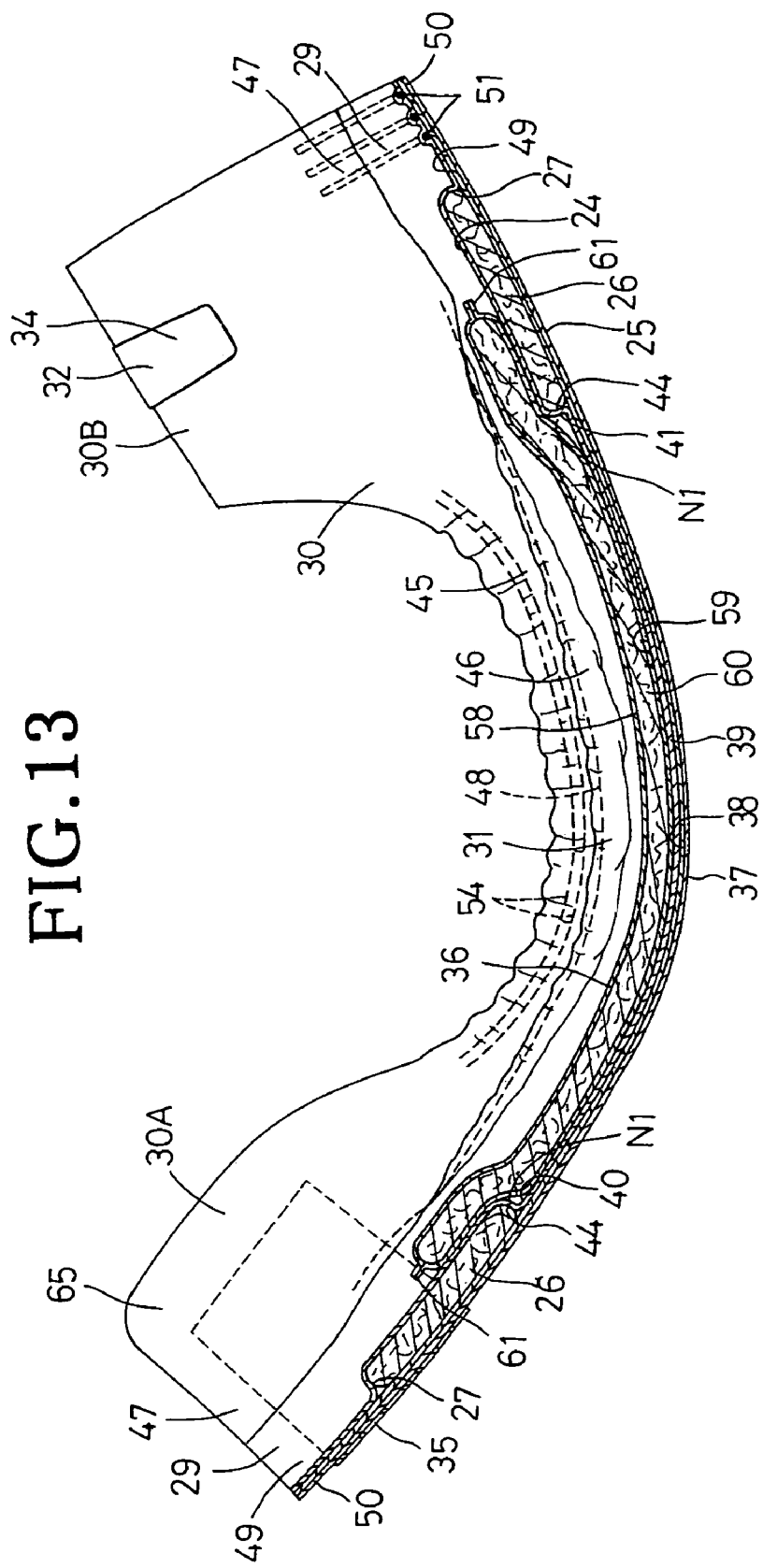
FIG. 13 is a sectional view taken along the line 13—13 in FIG. 11.
Figure 14:
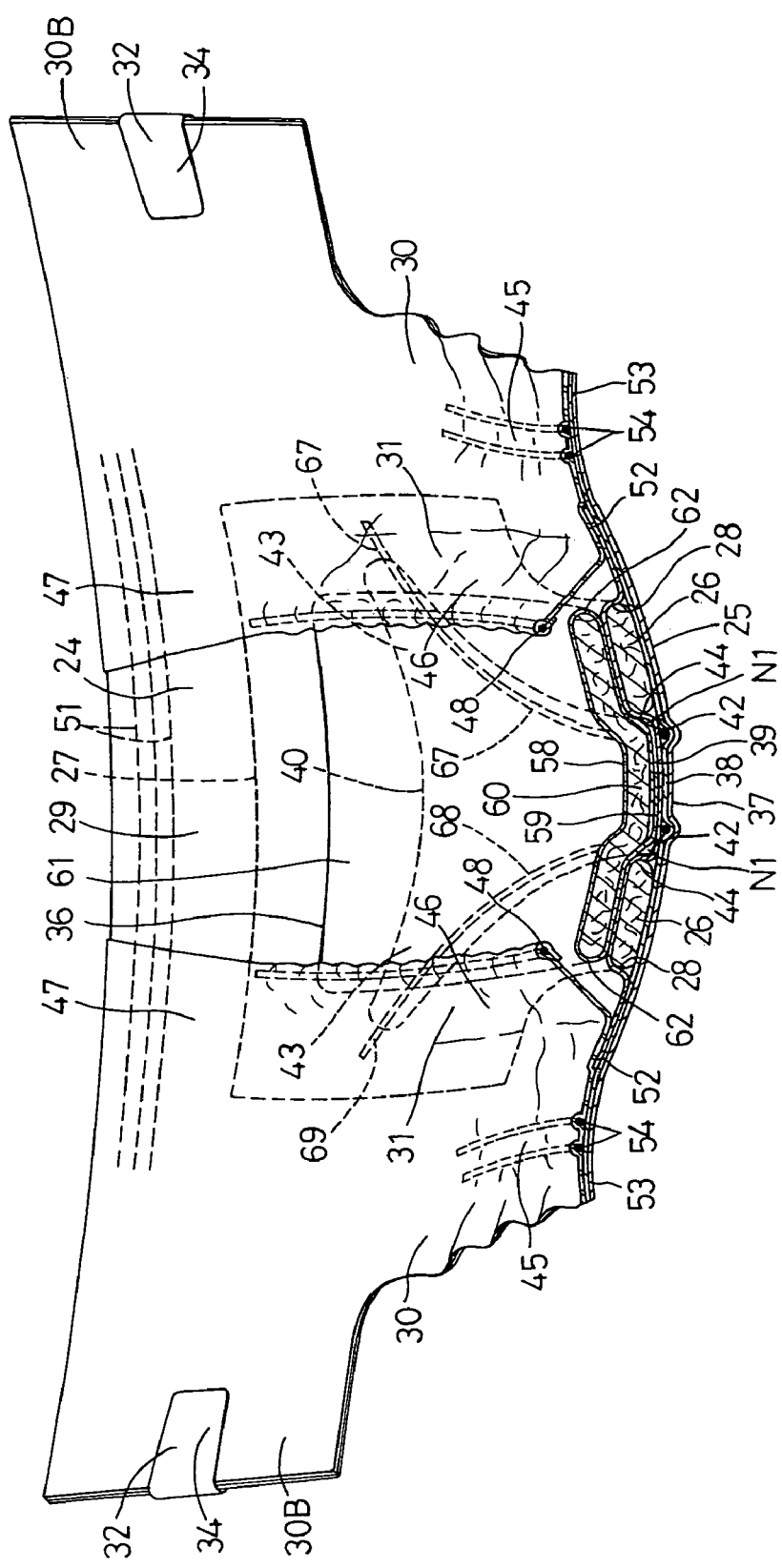
FIG. 14 is a sectional view taken along the line 14—14 in FIG. 11.

FIG. 11 is a perspective view showing a diaper 20C according to another preferred embodiment with a pad 36 laid in a pad seat 39, FIG. 12 is a partially cutaway plan view showing the diaper 20C of FIG. 11 with the pad 36 not shown, FIG. 13 is a sectional view taken along the line 13—13 in FIG. 11 and FIG. 14 is a sectional view taken along the line 14—14 in FIG. 11. In FIGS. 11 and 12, a transverse direction is indicated by an arrow L, a longitudinal direction is indicated by an arrow M and a thickness direction is indicated by an arrow N (in FIG. 11 alone). FIG. 12 shows the diaper 20C developed in the longitudinal direction as well as in the transverse direction against the contractile force of the stretch- and contractable elastic members 48, 51, 54, 66.

The diaper 20C is of open-type adapted to be worn with the front and rear waist regions 21, 23 connected to each other by means of the tape fasteners 32 after the body waste care pad 36 has been laid in the pad seat 39. Similarly to the diaper 20A of FIGS. 1–5, the diaper 20C also comprises the liquid-pervious topsheet 24, the liquid-impervious backsheet 25, the liquid-absorbent core 26 interposed between the top- and backsheets 24, 25 and extending between the front and rear waist regions 21, 23 and a pair of the liquid-impervious leak-barrier sheets 31 attached to the side flaps 30 so as to extending in the longitudinal direction. This diaper 20C is distinguished from the diaper 20A of FIGS. 1–5 in that the pad seat 39 has second extensions 66 and the pad seat 39 is provided with stretch- and contractable elastic members 67, 68. The remaining components similar to those in the diaper 20A of FIGS. 1–5 are designated by similar references and repetitive description thereof will be eliminated.

The elastic members 67, 68 are spaced from and opposed to each other and extend in the longitudinal direction. These elastic members 67, 68 extend over the pad seat 39 in the longitudinal direction to the first and second extensions 43, 66 wherein longitudinally opposite ends 69 of the respective elastic members 67, 68 extend on the lower surface of the cores 26 lying in the front and rear waist regions 21, 23. These elastic members 67, 68 respectively describe circular arcs which is convex inward as viewed in the transverse direction of the pad seat 39 so that a dimension by which these elastic members 67, 68 are spaced from each other in the transverse direction is minimized at a longitudinal middle of the pad seat 39. The elastic members 67, 68 are interposed between the top- and backsheets 24, 25 and bonded to the respective inner surfaces of these sheets 24, 25 with tension at a given ratio in the longitudinal direction. The longitudinally opposite ends 69 of these elastic members 67, 68 are interposed between the backsheet 25 and the core 26 and permanently bonded to the inner surface of the sheet 25.

The elastic members 67, 68 respectively describe circular arcs which is convex inward as viewed in the transverse direction of the pad seat 39 so that the contractile force of these elastic members 67, 68 may act fully on the pad seat 39 to raise the pad seat 39 as a whole toward the wearer's skin. Thus the pad 36 laid in the seat 39 can be fully pressed against the wearer's skin, ensuring body waste to be reliably absorbed and contained by the pad 36. The elastic members 67, 68 extend into the first and second extensions 43, 66 so that the tensile force transmitted to the first and second extensions 43, 66 in the course of wearing the diaper 20C as well as during use of the diaper 20C can be exerted on the elastic members 67, 68 via these extensions 43, 66 and thereby the elastic members 67, 68 can be stretched along curves of the wearer's crotch region. In this way, tightness of the pad seat 39 and contractile force of the elastic members 67, 68 acting on the pad seat 39 may be effectively utilized to hold the pad 36 against the wearer's skin.

The elastic members 67, 68 extend over the pad seat 39 in the longitudinal direction and the longitudinally opposite ends 69 of the respective elastic members 67, 68 extend on the lower surface of the cores 26 lying in the front and rear waist regions 21, 23. With such arrangement, the contractile force of these elastic members 67, 68 functions to press the cores 26 lying in the front and rear waist regions 21, 23 against the wearer's skin and thereby to hold these cores 26 in close contact with the wearer's skin. The diaper 20C ensures that body waste leaking out from the ends 61 of the pad 36, if occurs, can be absorbed and retained by the cores 26 lying in the front and rear waist regions 21, 23. Consequently, it is not apprehended that body waste might leak out from the diaper 20C.

Without departing from the scope of the present invention, it is possible to provide the pad seat 39 of the diaper 20A shown in FIGS. 1–5 with the elastic members 67, 68 similar to those used in the diaper 20B of FIGS. 6–10 or with the elastic members 67, 68 similar to those used in the diaper 20C of FIGS. 11–14. The pad seat 39 of the diaper 20A may have, in addition to a pair of the first extensions, a pair of the second extensions 66 bifurcated from the front end 40 of the pad seat 39 toward the corners defined by the crossing points of the end flaps 29 and the side flaps 30A in the front waist region 21. In the diaper 20B of FIGS. 6–10, the elastic members 67, 68 may be provided so as to describe circular arcs which are convex inward as viewed in the transverse direction of the pad seat 39.

These diapers 20A, 20B, 20C maybe alternatively arranged so that the pad seat 39 extends not only along the transverse middle of the crotch region 22 but also along the transverse middle of the front and rear waist regions 21, 23. In this case, the pad seat 39 preferably extends from the crotch region 22 into a rear half of the front waist region 21 and into a front half of the rear waist region 23. The diaper 20A, 20B, 20C may be also alternatively arranged so that, in the pad seat 39, the backsheet 25 extends along the inner peripheral wall 44 of the core 26 from the lower surface toward the upper surface of the core 26, the inner surface of the backsheet 25 is permanently bonded to the inner peripheral wall 44 of the core 26 and the top- and backsheets 24, 25 forming the pad seat 39 are permanently bonded to each other on the side of the upper surface of the core 26.

Stock materials for the topsheets 24, 58 is not limited to the hydrophilic fibrous nonwoven fabric but a hydrophobic fibrous nonwoven fabric having a plurality of fine apertures may be also used. Stock materials for the backsheet 25 is not limited to the composite nonwoven fabric but may be selected from the group consisting of a hydrophobic fibrous nonwoven fabric, breathable liquid-impervious plastic film and a composite sheet comprising two or more hydrophobic fibrous nonwoven fabric layers laminated together. It is possible without departing from the scope of the invention to form the backsheets 25, 59 and the leak-barrier sheets 31 using a composite nonwoven fabric (SMN·nonwoven fabric, SMS nonwoven fabric or SMMS nonwoven fabric) consisting of a melt blown fibrous nonwoven fabric having a high water-resistance and a spun bond fibrous nonwoven fabric being high in strength as well as in flexibility laminated on at least one side of the melt blown fibrous nonwoven fabric. The elastic members 48, 51, 54, 66 may be of natural or synthetic rubbers.

Stock materials for the fibrous nonwoven fabric layers may be selected from the group consisting of spun lace-, needle punch-, melt blown-, thermal bond-, spun bond- and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fibers selected from the group consisting of core-sheath conjugate fibers, side-by-side conjugate fibers, modified macaroni fibers, microporous fibers and fused type conjugate fibers.

Bonding of the top- and backsheets 24, 25 to each other, bonding of the core 26 to the sheets 24, 25, bonding of the leak-barrier sheets 31 to the sheets 24, 25, and securing of the elastic members 48, 51, 54, 66 to the sheets 24, 25, 31 may be achieved by using adhesives or welding technique such as heat-sealing or sonic sealing. Adhesives may be selected from the group consisting of a hot melt adhesive, acrylic adhesive and rubber-based adhesive.

The adhesives are coated on the topsheet 24, the backsheet 25 and the leak-barrier sheets 31 preferably in any one of spiral, wavy, zigzag, dotted or striped pattern. These sheets 24, 25, 31 may be coated with adhesives in such patterns to define adhesive-coated regions and adhesive-free regions in these sheets 24, 25, 31 and thereby to ensure that these sheets 24, 25, 31 are intermittently bonded one to another, the core 26 is intermittently bonded to the sheets 24, 25 and the elastic members 48, 51, 54, 66 are intermittently secured to the sheets 24, 25, 31.

What is claimed is:

1. An open-type disposable diaper having a front waist region, a rear waist region and a crotch region extending between said front and rear waist regions, said diaper comprising:
   a liquid-pervious topsheet;
   a liquid-impervious backsheet;
   a liquid-absorbent core between said sheets and extending between said front and rear waist regions;
   a pair of end flaps extending in a transverse direction outside longitudinally opposite ends of said core;
   a pair of side flaps extending in a longitudinal direction outside transversely opposite side edges of said core;
   tape fasteners attached to said side flaps in said rear waist region so as to extend in the transverse direction, wherein said diaper is adapted to be worn with a body waste care pad laid on said topsheet and with said tape fasteners being anchored on an outer surface of said front waist region to connect said front and rear waist regions with each other; and
   at least one of said front and rear waist regions and said crotch region being provided along a transverse middle thereof with a pad seat formed by a cavity defined in a middle zone of said core and portions of said topsheet and backsheet located in said cavity, said pad seat including a pair of first extensions wherein a rear end of said pad seat lying on a side of said rear waist region is bifurcated into said first extensions which extend toward said tape fasteners.

2. The diaper as defined by claim 1, wherein said pad seat further includes a pair of second extensions; and
   a front end of said pad seat lying on a side of said front waist region is bifurcated into said second extensions which extend respectively toward a pair of corners defined by crossing points of the end flaps and the side flaps in said front waist region.

3. The diaper as defined by claim 1, wherein said pad seat is provided in a vicinity of side edges thereof with stretchable and contractible elastic members contractibly secured to said pad seat and extending in the longitudinal direction.

4. The diaper as defined by claim 3, wherein said elastic members fully extend over said pad seat and longitudinally opposite ends of said elastic members extend under lower surfaces of respective portions of said core in said front and rear waist regions.

5. The diaper as defined by claim 3, wherein said elastic members respectively describe arcs which are convex inward as viewed in the transverse direction of said pad seat so that a distance at which said elastic members are spaced from each other in the transverse direction is minimum at a longitudinal middle of said pad seat.

6. The diaper as defined by claim 3, wherein
   said pad seat further includes a pair of second extensions;
   a front end of said pad seat lying on a side of said front waist region is bifurcated into said second extensions which extend respectively toward a pair of corners defined by crossing points of the end flaps and the side flaps in said front waist region; and
   each of said elastic members extends into one of the first extensions and one of the second extensions of said pad seat.

7. The diaper as defined by claim 3, wherein said elastic members have a tensile stress in a range of 0.05 to 4.0 N.

8. The diaper as defined by claim 1, wherein
   said topsheet extends along an inner peripheral wall of said core surrounding said pad seat from an upper surface of said core toward a lower surface of said core,
   the portions of said topsheet and backsheet constituting said pad seat are bonded to each other at a level of the lower surface of said core, and
   a difference in level in proportion to a thickness dimension of said core is formed between the upper surface of said core and said pad seat.

9. The diaper as defined by claim 3, wherein said elastic members are sandwiched between and attached to at least one of said topsheet and backsheet.

10. The diaper as defined by claim 3, wherein said elastic members bias said pad seat upwardly in a thickness direction from the backsheet toward the topsheet, for pressing the body waste care pad against a wearer's skin, in use.

11. An open-type disposable diaper having a front waist region, a rear waist region and a crotch region extending between said front and rear waist regions, said diaper comprising:
    a liquid-pervious topsheet;
    a liquid-impervious backsheet;
    a liquid-absorbent core between said sheets and extending between said front and rear waist regions;
    a pair of end flaps extending in a transverse direction outside longitudinally opposite ends of said core;
    a pair of side flaps extending in a longitudinal direction outside transversely opposite side edges of said core;
    a body waste care pad laid on said topsheet;
    tape fasteners attached to said side flaps in said rear waist region so as to extend in the transverse direction, wherein said diaper is adapted to be worn with said body waste care pad laid on said topsheet and with said tape fasteners being anchored on an outer surface of said front waist region to connect said front and rear waist regions with each other; and
    at least one of said front and rear waist regions and said crotch region being provided along a transverse middle thereof with a pad seat formed by a cavity defined in a middle zone of said core and portions of said topsheet and backsheet located in said cavity, said pad seat including a pair of first extensions wherein a rear end of said pad seat lying on a side of said rear waist region is bifurcated into said first extensions which extend toward said tape fasteners.

12. The diaper as defined by claim 11, wherein
said pad seat is provided in a vicinity of side edges thereof with stretchable and contractible elastic members contractibly secured to said pad seat and extending in the longitudinal direction; and
said elastic members are sandwiched between and attached to at least one of said topsheet and backsheet.

13. The diaper as defined by claim 12, wherein said elastic members bias said pad seat upwardly in a thickness direction from the backsheet toward the topsheet, for pressing said body waste care pad against a wearer's skin, in use.

14. The diaper as defined by claim 11, wherein said body waste care pad has a transversely middle portion received in said pad seat and depressed downwardly in a thickness direction from the topsheet toward the backsheet.

15. The diaper as defined by claim 11, wherein said first extensions of said pad seat extend in the transverse direction beyond transversely opposite side edges of said body waste care pad being partially received in said pad seat.

16. The diaper as defined by claim 1, wherein said absorbent core comprises liquid absorbing material and said pad seat is free of said liquid absorbing material.

17. The diaper as defined by claim 16, wherein
said pad seat is provided in a vicinity of side edges thereof with stretchable and contractible elastic members contractibly secured to said pad seat; and
said elastic members are sandwiched between and attached to at least one of said topsheet and backsheet.

18. The diaper as defined by claim 17, wherein the elastic members are completely located within a boundary of said pad seat.

19. The diaper as defined by claim 17, wherein each of the elastic members has
a crotch portion extending in the longitudinal direction; and
a rear end portion extending rearwardly from the crotch portion, obliquely to the longitudinal direction, and towards one of said fasteners.

20. The diaper as defined by claim 19, wherein a terminal end of the rear end portion of each of the elastic members is located under the liquid absorbing material of said absorbent core.

* * * * *